United States Patent [19]

Mallonee

[11] Patent Number: 5,175,094
[45] Date of Patent: * Dec. 29, 1992

[54] INCREASED EXPRESSION OF HBCAG

[75] Inventor: Richard L. Mallonee, Catonsville, Md.

[73] Assignee: Becton Dickinson and Company, Franklin Lakes, N.J.

[*] Notice: The portion of the term of this patent subsequent to Dec. 22, 2009 has been disclaimed.

[21] Appl. No.: 739,643

[22] Filed: Aug. 1, 1991

[51] Int. Cl.$^5$ ............................................. C12P 21/02
[52] U.S. Cl. .................................................... 435/69.3
[58] Field of Search ................ 435/69.3, 172.1, 252.3, 435/320.1; 935/22, 29, 33, 38, 39, 66, 73

[56] References Cited

U.S. PATENT DOCUMENTS 4,710,463  12/1987  Murray ............................. 435/69.3

FOREIGN PATENT DOCUMENTS 0182442  5/1986  European Pat. Off. .
0271302  6/1988  European Pat. Off. .
0272483  6/1988  European Pat. Off. .
0304238  2/1989  European Pat. Off. .

OTHER PUBLICATIONS

Yie et al. "High level expression of HBcAg in *E. coli* by modification of the 5'end of the HBc gene" Chinese Journal of Virology 4(4):312-318 (1988).

Kim et al. "Expression and Secretion of Hepatitis B Viral Mutant Cure Antigen" Korean Journal of Microbiology 27(3):169-175 (1989).

Grosjean et al. "Preferential codon usage in prokaryotic genes: the optimal condon-anticodon interaction energy and the selective codon usage in efficiently expressed genes" Gene 18:199-209 (1982).

R. A. Bhat et al., *Hepatology* 11:271 (1989).
R. E. Lanford et al., *Viral Immunology* 1:97 (1987).

*Primary Examiner*—Richard A. Schwartz
*Assistant Examiner*—Michelle Johnson
*Attorney, Agent, or Firm*—Brian K. Stierwalt

[57] ABSTRACT

The invention relates to increased expression of HBcAg. Methods are disclosed which exhibit increased levels of expression of HBcAg. Increased levels of expression is also achieved by various modifications of the HBcAg sequence.

13 Claims, 1 Drawing Sheet

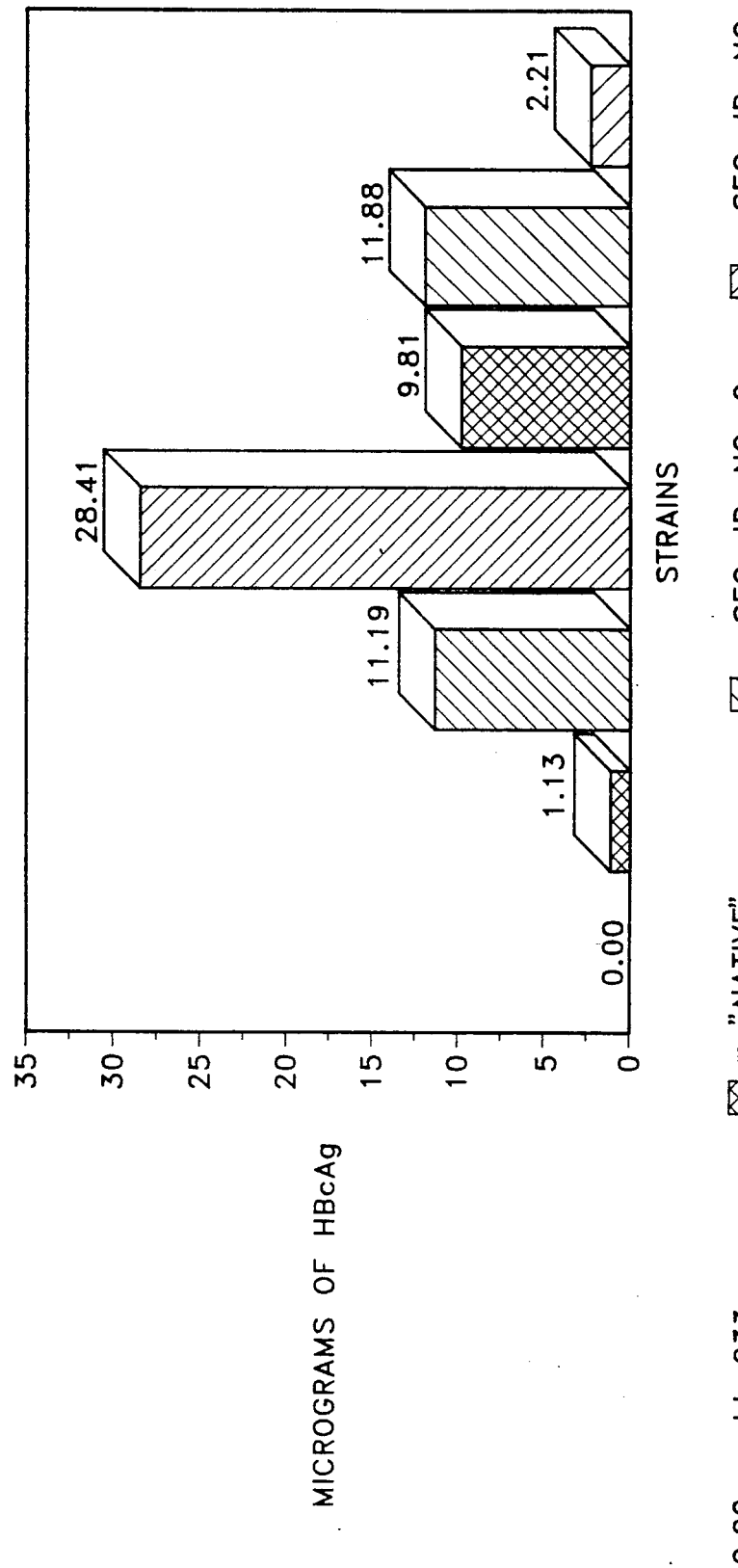

INCREASED EXPRESSION OF HBCAG

FIELD OF THE INVENTION

The invention is in the field of molecular biology. In particular, the invention relates to new sequences and improved expression of hepatitis B core protein.

BACKGROUND OF THE INVENTION

Hepatitis B virus is the most thoroughly characterized pathogen of the hepatitis diseases. The hepatitis B virus is associated with a wide spectrum of liver disease, from a subclinical carrier state to accute hepatitis, chronic hepatitis, postnecrotic (posthepatitic) cirrhosis, and hepatocellular carcinoma. It also has a poorly understood association with several primary non hepatic disorders including polyarteritis nodesa and other collagen vascular diseases, membraneous glomerulonephritis, essential mixed cryoglobulinemina and papular acrodermatitis of childhood. Hepatitis symptoms and signs vary from minor flu like illnesses to fulminant, fatal liver failure.

Groups at risk for contracting hepatitis B virus include certain hospital and dentist staff (e.g., oncology, hemodialysis-transplantation, gastroenterology, intensive care units, diagnostic laboratories, and surgical units), staff in institutions for the mentally handicapped, patients receiving blood and blood products, drug addicts, male homosexuals, and the families of chronic carriers.

The infective "DANE" particle consists of an inner core plus an outer surface coat. The inner core contains DNA and DNA polymerase. The DNA replicates within the nuclei of infected hepatocytes. The core antigen (HBcAg) is associated with the viral inner core. It can be found in infected liver cells but is not detectable in serum except by special techniques which disrupt the DANE particle. The hepatitis B virus is present in the cytoplasm of parenchymal liver cells of individuals with hepatitis B and constitutes the infective virus. The core particle displays HBcAg. The core of this particle is found in the nucleus of parenchymal cells, but as it passes through the cytoplasm, it acquires a surface coat.

Antibody to the core antigen appears promptly in the blood of infected individuals and persists indefinitely. High titers of IgM anti-HBc is found in patients with accute disease and may be the only marker of accute hepatitis B in some situations.

Serological detection of anti HBc is accepted diagnostic evidence of hepatitis B viral infection. Therefore, it is desirable to have substantial quantities of HBcAg for use as an immunogen in development of monoclonal and polyclonal antibodies to the HBcAg, for preparing vaccines, and for use in detection of the viral infection in patients.

SUMMARY OF THE INVENTION

The present invention provides new HBcAg sequences with improved expression. The invention also provides nucleotide sequences which enhance expression of HBcAg. The invention also provides new HBcAg protein sequences. In addition, the invention provides methods for increasing expression of HBcAg.

BRIEF DESCRIPTION OF THE FIGURES

FIG. 1 Enzyme linked immunosorbent Assay (ELISA) data showing increased expression of HBcAg with sequences of the invention.

DETAILED DESCRIPTION

The present invention provides new HBcAg sequences and methods for increasing expression of HBcAg. When Sequence ID No: 1 is altered to include additional nucleotides between the ribosome binding site and start codon, (also referred to as the initiation codon), the expression level is about ten (10) times higher than the same sequence unmodified. When the modification involves changing the second codon (first codon after the start codon) from GAC to GCT, plus nucleotides between the ribosome binding site and first ATG codon, increases of about twenty-five (25) times higher expression are obtained over the native sequence.

The present invention also provides DNA molecules described in Sequence ID No: 3, Sequence ID No: 5, Sequence ID No: 7, Sequence ID No: 9, and Sequence ID No: 11.

The invention also provides hosts, and methods for increasing expression of HBcAg which comprises transforming a host with the disclosed sequences.

The invention also provides amino acid sequences described in Sequence ID No: 2, Sequence ID No: 4, Sequence ID No: 6, Sequence ID No: 8, Sequence ID No: 10, and Sequence ID No: 12 and kits comprising the sequences.

Sequence ID No: 1 is referred to as the "native" sequence. Preferably Sequence ID No: 1 has an eight base pair spacer between the ribosome binding site and start codon. Most preferably the eight base pair spacer is Sequence ID No: 14 (AACAGACC). Sequence ID No: 3 is the same as Sequence ID No: 1 (silent mutations from a G to A at bp 39 and a C to T at bp 249 are present). Preferably Sequence ID No: 3 has a 10 base pair spacer between the ribosome binding site and the start codon. Most preferably the ten base pair spacer is Sequence ID No: 13 (AACAGAATTC). Sequence ID No: 5 is the same as Sequence ID No: 1 but has the alterations of the second codon change, bp 467 changes from G to A and deletion of bp 468, causing a frameshift. Preferably Sequence ID No: 5 has a ten base pair spacer between the ribosome binding site and start codon. Most preferably the ten base pair spacer is Sequence ID No: 13. Sequence ID No: 7 is the same as Sequence ID No: 1 but has the second codon change. Preferably Sequence ID No: 7 has an eight base pair spacer between the ribosome binding site and start codon. Most preferably the eight base pair spacer is Sequence ID No: 14. Sequence ID No: 9 is the same as Sequence ID No: 7 with a transition at bp 359 from a T to a C (resulting in a Val to Ala change in the protein). Preferably Sequence ID No: 9 has a ten base pair spacer between the ribosome binding site and start codon. Most preferably the ten base pair spacer is Sequence ID No: 13. Sequence ID No: 11 is the same as Sequence ID No: 7 with alterations of the second codon change, and deletion of bp 455, causing a frameshift. Preferably an eight base pair spacer is between the ribosome binding site and start codon. Most preferably the eight base pair spacer is Sequence ID No: 14.

Sequence ID No: 2, 4, 6, 8, 10, and 12 are predicted HBcAg protein sequences of the invention. Sequence ID No: 1 encodes the protein of Sequence ID No: 2.

Sequence ID No: 3 also encodes the protein sequence in Sequence ID No: 2 (or 4). Sequence ID No: 5 encodes the protein in Sequence ID No: 6. Sequence ID No: 7 encodes the protein in Sequence ID No: 8. Sequence ID No: 9 encodes the protein in Sequence ID No: 10 Sequence ID No: 11 encodes the protein in Sequence ID No: 12. Since many amino acids are selected by more than one codon (degeneracy), DNA sequences can vary without corresponding changes in the amino acid sequences.

Tables 1 through 11 depict nucleotide and amino acid sequences of the invention (nucleotide sequences left to right are 5' to 3' and amino acid sequences left to right are amino terminus to carboxy terminus).

TABLE 1

| | | | | | | |
|---|---|---|---|---|---|---|
| ATGGACATTG | ACCCTTATAA | AGAATTTGGA | GCTACTGTGG | AGTTACTCTC | GTTTTTGCCT | 60 |
| TCTGACTTCT | TTCCTTCCGT | CAGAGATCTC | CTAGACACCG | CCTCAGCTCT | GTATCGGGAA | 120 |
| GCCTTAGAGT | CTCCTGAGCA | TTGCTCACCT | CACCATACCG | CACTCAGGCA | AGCCATTCTC | 180 |
| TGCTGGGGGG | AATTGATGAC | TCTAGCTACC | TGGGTGGGTA | ATAATTTGGA | AGATCCAGCA | 240 |
| TCAAGGGACC | TAGTAGTCAA | TTATGTTAAT | ACTAACATGG | GTTTAAAAAT | TAGGCAACTA | 300 |
| TTGTGGTTTC | ATATATCTTG | CCTTACTTTT | GGAAGAGAGA | CTGTACTTGA | ATATTTGGTC | 360 |
| TCTTTCGGAG | TGTGGATTCG | CACTCCTCCA | GCCTATAGAC | CACCAAATGC | CCCTATCTTA | 420 |
| TCAACACTTC | CGGAAACTAC | TGTTGTTAGA | CGACGGGACC | GAGGCAGGTC | CCCTAGAAGA | 480 |
| AGAACTCCCT | CGCCTCGCAG | ACGCAGATCT | CAATCGCCGC | GTCGCAGAAG | ATCTCAATCT | 540 |
| CGGGAATCTC | AATGTTAG | | | | | 558 |

TABLE 2

| | | | | | | |
|---|---|---|---|---|---|---|
| ATGGACATTG | ACCCTTATAA | AGAATTTGGA | GCTACTGTAG | AGTTACTCTC | GTTTTTGCCT | 60 |
| TCTGACTTCT | TTCCTTCCGT | CAGAGATCTC | CTAGACACCG | CCTCAGCTCT | GTATCGGGAA | 120 |
| GCCTTAGAGT | CTCCTGAGCA | TTGCTCACCT | CACCATACCG | CACTCAGGCA | AGCCATTCTC | 180 |
| TGCTGGGGGG | AATTGATGAC | TCTAGCTACC | TGGGTGGGTA | ATAATTTGGA | AGATCCAGCA | 240 |
| TCAAGGGATC | TAGTAGTCAA | TTATGTTAAT | ACTAACATGG | GTTTAAAAAT | TAGGCAACTA | 300 |
| TTGTGGTTTC | ATATATCTTG | CCTTACTTTT | GGAAGAGAGA | CTGTACTTGA | ATATTTGGCC | 360 |
| TCTTTCGGAG | TGTGGATTCG | CACTCCTCCA | GCCTATAGAC | CACCAAATGC | CCCTATCTTA | 420 |
| TCAACACTTC | CGGAAACTAC | TGTTGTTAGA | CGACGGGACC | GAGGCAGGTC | CCCTAGAAGA | 480 |
| AGAACTCCCT | CGCCTCGCAG | ACGCAGATCT | CAATCGCCGC | GTCGCAGAAG | ATCTCAATCT | 540 |
| CGGGAATCTC | AATGTTAG | | | | | 558 |

TABLE 3

| | | | | | | |
|---|---|---|---|---|---|---|
| ATGGCTATTG | ACCCTTATAA | AGAATTTGGA | GCTACTGTGG | AGTTACTCTC | GTTTTTGCCT | 60 |
| TCTGACTTCT | TTCCTTCCGT | CAGAGATCTC | CTAGACACCG | CCTCAGCTCT | GTATCGGGAA | 120 |
| GCCTTAGAGT | CTCCTGAGCA | TTGCTCACCT | CACCATACCG | CACTCAGGCA | AGCCATTCTC | 180 |
| TCGTGGGGGG | AATTGATGAC | TCTAGCTACC | TGGGTGGGTA | ATAATTTGGA | AGATCCAGCA | 240 |
| TCAAGGGACC | TAGTAGTCAA | TTATGTTAAT | ACTAACATGG | GTTTAAAAAT | TAGGCAACTA | 300 |
| TTGTGGTTTC | ATATATCTTG | CCTTACTTTT | GGAAGAGAGA | CTGTACTTGA | ATATTTGGTC | 360 |
| TCTTTCGGAG | TGTGGATTCG | CACTCCTCCA | GCCTATAGAC | CACCAAATGC | CCCTATCTTA | 420 |
| TCAACACTTC | CGGAAACTAC | TGTTGTTAGA | CGACGGGACC | GAGGCAATCC | CCTAGAAGAA | 480 |
| GAACTCCCTC | GCCTCGCAGA | CGCAGATCTC | AATCGCCGCG | TCGCAGAAGA | TCTCAATCTC | 540 |
| GGGAATCTCA | ATGTTAGAAG | CTTCCGACAA | AACCGCCTAC | TCTCTTCTAA | AAGTCGGACT | 600 |
| ATGTCTAATT | TAGTCTTGCG | TCTTCGCCAG | ACTATTTTGT | CTTAA | | 645 |

TABLE 4

| | | | | | | |
|---|---|---|---|---|---|---|
| ATGGCTATTG | ACCCTTATAA | AGAATTTGGA | GCTACTGTGG | AGTTACTCTC | GTTTTTGCCT | 60 |
| TCTGACTTCT | TTCCTTCCGT | CAGAGATCTC | CTAGACACCG | CCTCAGCTCT | GTATCGGGAA | 120 |
| GCCTTAGAGT | CTCCTGAGCA | TTGCTCACCT | CACCATACCG | CACTCAGGCA | AGCCATTCTC | 180 |
| TGCTGGGGGG | AATTGATGAC | TCTAGCTACC | TGGGTGGGTA | ATAATTTGGA | AGATCCAGCA | 240 |
| TCAAGGGACC | TAGTAGTCAA | TTATGGTAAT | ACTAACATGG | GTTTAAAAAT | TAGGCAACTA | 300 |
| TTGTGGTTTC | ATATATCTTG | CCTTACTTTT | GGAAGAGAGA | CTGTACTTGA | ATATTTGGTC | 360 |
| TCTTTCGGAG | TGTGGATTCG | CACTCCTCCA | GCCTATAGAC | CACCAAATGC | CCCTATCTTA | 420 |
| TCAACACTTC | CGGAAACTAC | TGTTGTTAGA | CGACGGGACC | GAGGCAGGTC | CCCTAGAAGA | 480 |
| AGAACTCCCT | CGCCTCGCAG | ACGCAGATCT | CAATCGCCGC | GTCGCAGAAG | ATCTCAATCT | 540 |
| CGGGAATCTC | AATGTTAG | | | | | 558 |

TABLE 5

| | | | | | | |
|---|---|---|---|---|---|---|
| ATGGCTATTG | ACCCTTATAA | AGAATTTGGA | GCTACTGTGG | AGTTACTCTC | GTTTTTGCCT | 60 |
| TCTGACTTCT | TTCCTTCCGT | CAGAGATCTC | CTAGACACCG | CCTCAGCTCT | GTATCGGGAA | 120 |
| GCCTTAGAGT | CTCCTGAGCA | TTGCTCACCT | CACCATACCG | CACTCAGGCA | AGCCATTCTC | 180 |
| TGCTGGGGGG | AATTGATGAC | TCTAGCTACC | TGGGTGGGTA | ATAATTTGGA | AGATCCAGCA | 240 |
| TCAAGGGACC | TAGTAGTCAA | TTATGTTAAT | ACTAACATGG | GTTTAAAAAT | TAGGCAACTA | 300 |
| TTGTGGTTTC | ATATATCTTG | CCTTACTTTT | GGAAGAGAGA | CTGTACTTGA | ATATTTGGCC | 360 |
| TCTTTCGGAG | TGTGGATTCG | CACTCCTCCA | GCCTATAGAC | CACCAAATGC | CCCTATCTTA | 420 |
| TCAACACTTC | CGGAAACTAC | TGTTGTTAGA | CGACGGGACC | GAGGCAGGTC | CCCTAGAAGA | 480 |
| AGAACTCCCT | CGCCTCGCAG | ACGCAGATCT | CAATCGCCGC | GTCGCAGAAG | ATCTCAATCT | 540 |
| CGGGAATCTC | AATGTTAG | | | | | 558 |

TABLE 6

| | | | | | | |
|---|---|---|---|---|---|---|
| ATGGCTATTG | ACCCTTATAA | AGAATTTGGA | GCTACTGTGG | AGTTACTCTC | GTTTTTGCCT | 60 |
| TCTGACTTCT | TTCCTTCCGT | CAGAGATCTC | CTAGACACCG | CCTCAGCTCT | GTATCGGGAA | 120 |
| GCCTTAGAGT | CTCCTGAGCA | TTGCTCACCT | CACCATACCG | CACTCAGGCA | AGCCATTCTC | 180 |

TABLE 6-continued

| | | | | | | |
|---|---|---|---|---|---|---|
| TGCTGGGGGG | AATTGATGAC | TCTAGCTACC | TGGGTGGGTA | ATAATTTGGA | AGATCCAGCA | 240 |
| TCAAGGGACC | TAGTAGTCAA | TTATGTTAAT | ACTAACATGG | GTTTAAAAAT | TAGGCAACTA | 300 |
| TTGTGGTTTC | ATATATCTTG | CCTTACTTTT | GGAAGAGAGA | CTGTACTTGA | ATATTTGGTC | 360 |
| TCTTTCGGAG | TGTGGATTCG | CACTCCTCCA | GCCTATAGAC | CACCAAATGC | CCCTATCTTA | 420 |
| TCAACACTTC | CGGAAACTAC | TGTTGTTAGA | CGACGGACCG | AGGCAGGTCC | CCTAGAAGAA | 480 |
| GAACTCCCTC | GCCTCGCAGA | CGCAGATCTC | AATCGCCGCG | TCGCAGAAGA | TCTCAATCTC | 540 |
| GGGAATCTCA | ATGTTAGAAG | CTTCCGACAA | AACCGCCTAC | TCTCTTCTAA | AAGTCGGACT | 600 |
| ATGTCTAATT | TAGTCTTGCG | TCTTCGCCAG | ACTATTTTGT | CTTAA | | 645 |

TABLE 7

| | | | | | | | | | | | | | | |
|---|---|---|---|---|---|---|---|---|---|---|---|---|---|---|
| Met 1 | Asp | Ile | Asp | Pro 5 | Tyr | Lys | Glu | Phe | Gly 10 | Ala | Thr | Val | Glu | Leu 15 | Leu |
| Ser | Phe | Leu | Pro 20 | Ser | Asp | Phe | Phe | Pro 25 | Ser | Val | Arg | Asp | Leu 30 | Leu | Asp |
| Thr | Ala | Ser 35 | Ala | Leu | Tyr | Arg | Glu 40 | Ala | Leu | Glu | Ser | Pro 45 | Glu | His | Cys |
| Ser | Pro 50 | His | His | Thr | Ala | Leu 55 | Arg | Gln | Ala | Ile | Leu 60 | Cys | Trp | Gly | Glu |
| Leu 65 | Met | Thr | Leu | Ala | Thr 70 | Trp | Val | Gly | Asn | Asn 75 | Leu | Glu | Asp | Pro | Ala 80 |
| Ser | Arg | Asp | Leu | Val 85 | Val | Asn | Tyr | Val | Asn 90 | Thr | Asn | Met | Gly | Leu 95 | Lys |
| Ile | Arg | Gln | Leu 100 | Leu | Trp | Phe | His | Ile 105 | Ser | Cys | Leu | Thr | Phe 110 | Gly | Arg |
| Glu | Thr | Val 115 | Leu | Glu | Tyr | Leu | Val 120 | Ser | Phe | Gly | Val | Trp 125 | Ile | Arg | Thr |
| Pro | Pro 130 | Ala | Tyr | Arg | Pro | Pro 135 | Asn | Ala | Pro | Ile | Leu 140 | Ser | Thr | Leu | Pro |
| Glu 145 | Thr | Thr | Val | Val | Arg 150 | Arg | Arg | Asp | Arg | Gly 155 | Arg | Ser | Pro | Arg | Arg 160 |
| Arg | Thr | Pro | Ser | Pro 165 | Arg | Arg | Arg | Arg | Ser 170 | Gln | Ser | Pro | Arg | Arg 175 | Arg |
| Arg | Ser | Gln | Ser 180 | Arg | Glu | Ser | Gln | Cys 185 | | | | | | | |

TABLE 8

| | | | | | | | | | | | | | | |
|---|---|---|---|---|---|---|---|---|---|---|---|---|---|---|
| Met 1 | Ala | Ile | Asp | Pro 5 | Tyr | Lys | Glu | Phe | Gly 10 | Ala | Thr | Val | Glu | Leu 15 | Leu |
| Ser | Phe | Leu | Pro 20 | Ser | Asp | Phe | Phe | Pro 25 | Ser | Val | Arg | Asp | Leu 30 | Leu | Asp |
| Thr | Ala | Ser 35 | Ala | Leu | Tyr | Arg | Glu 40 | Ala | Leu | Glu | Ser | Pro 45 | Glu | His | Cys |
| Ser | Pro 50 | His | His | Thr | Ala | Leu 55 | Arg | Gln | Ala | Ile | Leu 60 | Cys | Trp | Gly | Glu |
| Leu 65 | Met | Thr | Leu | Ala | Thr 70 | Trp | Val | Gly | Asn | Asn 75 | Leu | Glu | Asp | Pro | Ala 80 |
| Ser | Arg | Asp | Leu | Val 85 | Val | Asn | Tyr | Val | Asn 90 | Thr | Asn | Met | Gly | Leu 95 | Lys |
| Ile | Arg | Gln | Leu 100 | Leu | Trp | Phe | His | Ile 105 | Ser | Cys | Leu | Thr | Phe 110 | Gly | Arg |
| Glu | Thr | Val 115 | Leu | Glu | Tyr | Leu | Val 120 | Ser | Phe | Gly | Val | Trp 125 | Ile | Arg | Thr |
| Pro | Pro 130 | Ala | Tyr | Arg | Pro | Pro 135 | Asn | Ala | Pro | Ile | Leu 140 | Ser | Thr | Leu | Pro |
| Glu 145 | Thr | Thr | Val | Val | Arg 150 | Arg | Arg | Asp | Arg | Gly 155 | Arg | Ser | Pro | Arg | Arg 160 |
| Arg | Thr | Pro | Ser | Pro 165 | Arg | Arg | Arg | Arg | Ser 170 | Gln | Ser | Pro | Arg | Arg 175 | Arg |
| Arg | Ser | Gln | Ser 180 | Arg | Glu | Ser | Gln | Cys 185 | | | | | | | |

TABLE 9

| | | | | | | | | | | | | | | |
|---|---|---|---|---|---|---|---|---|---|---|---|---|---|---|
| Met 1 | Ala | Ile | Asp | Pro 5 | Tyr | Lys | Glu | Phe | Gly 10 | Ala | Thr | Val | Glu | Leu 15 | Leu |
| Ser | Phe | Leu | Pro 20 | Ser | Asp | Phe | Phe | Pro 25 | Ser | Val | Arg | Asp | Leu 30 | Leu | Asp |
| Thr | Ala | Ser 35 | Ala | Leu | Tyr | Arg | Glu 40 | Ala | Leu | Glu | Ser | Pro 45 | Glu | His | Cys |
| Ser | Pro 50 | His | His | Thr | Ala | Leu 55 | Arg | Gln | Ala | Ile | Leu 60 | Cys | Trp | Gly | Glu |
| Leu 65 | Met | Thr | Leu | Ala | Thr 70 | Trp | Val | Gly | Asn | Asn 75 | Leu | Glu | Asp | Pro | Ala 80 |
| Ser | Arg | Asp | Leu | Val 85 | Val | Asn | Tyr | Val | Asn 90 | Thr | Asn | Met | Gly | Leu 95 | Lys |
| Ile | Arg | Gln | Leu 100 | Leu | Trp | Phe | His | Ile 105 | Ser 110 | Cys | Leu | Thr | Phe | Gly | Arg |

TABLE 9-continued

| Glu | Thr | Val 115 | Leu | Glu | Tyr | Leu | Ala 120 | Ser | Phe | Gly | Val | Trp 125 | Ile | Arg | Thr |
|---|---|---|---|---|---|---|---|---|---|---|---|---|---|---|---|
| Pro | Pro 130 | Ala | Tyr | Arg | Pro | Pro 135 | Asn | Ala | Pro | Ile | Leu 140 | Ser | Thr | Leu | Pro |
| Glu 145 | Thr | Thr | Val | Val | Arg 150 | Arg | Arg | Asp | Arg | Gly 155 | Arg | Ser | Pro | Arg | Arg 160 |
| Arg | Thr | Pro | Ser | Pro 165 | Arg | Arg | Arg | Arg | Ser 170 | Gln | Ser | Pro | Arg | Arg 175 | Arg |
| Arg | Ser | Gln | Ser 180 | Arg | Glu | Ser | Gln | Cys 185 | | | | | | | |

TABLE 10

| Met 1 | Ala | Ile | Asp | Pro 5 | Tyr | Lys | Glu | Phe | Gly 10 | Ala | Thr | Val | Glu | Leu 15 | Leu |
|---|---|---|---|---|---|---|---|---|---|---|---|---|---|---|---|
| Ser | Phe | Leu | Pro 20 | Ser | Asp | Phe | Phe | Pro 25 | Ser | Val | Arg | Asp | Leu 30 | Leu | Asp |
| Thr | Ala | Ser 35 | Ala | Leu | Tyr | Arg | Glu 40 | Ala | Leu | Glu | Ser | Pro 45 | Glu | His | Cys |
| Ser | Pro 50 | His | His | Thr | Ala | Leu 55 | Arg | Gln | Ala | Ile | Leu 60 | Cys | Trp | Gly | Glu |
| Leu 65 | Met | Thr | Leu | Ala | Thr 70 | Trp | Val | Gly | Asn | Asn 75 | Leu | Glu | Asp | Pro | Ala 80 |
| Ser | Arg | Asp | Leu | Val 85 | Val | Asn | Tyr | Val | Asn 90 | Thr | Asn | Met | Gly | Leu 95 | Lys |
| Ile | Arg | Gln | Leu 100 | Leu | Trp | Phe | His | Ile 105 | Ser | Cys | Leu | Thr | Phe 110 | Gly | Arg |
| Glu | Thr | Val 115 | Leu | Glu | Tyr | Leu | Val 120 | Ser | Phe | Gly | Val | Trp 125 | Ile | Arg | Thr |
| Pro | Pro 130 | Ala | Tyr | Arg | Pro | Pro 135 | Asn | Ala | Pro | Ile | Leu 140 | Ser | Thr | Leu | Pro |
| Glu 145 | Thr | Thr | Val | Val | Arg 150 | Arg | Arg | Asp | Arg | Gly 155 | Asn | Pro | Leu | Glu | Glu 160 |
| Glu | Leu | Pro | Arg | Leu 165 | Ala | Asp | Ala | Asp | Leu 170 | Asn | Arg | Arg | Val | Ala 175 | Glu |
| Asp | Leu | Asn | Leu 180 | Gly | Asn | Leu | Asn | Val 185 | Arg | Ser | Phe | Arg | Gln 190 | Asn | Arg |
| Leu | Leu | Ser 195 | Ser | Lys | Ser | Arg | Thr 200 | Met | Ser | Asn | Leu | Val 205 | Leu | Arg | Leu |
| Arg | Gln 210 | Thr | Ile | Leu | Ser | | | | | | | | | | |

TABLE 11

| Met 1 | Ala | Ile | Asp | Pro 5 | Tyr | Lys | Glu | Phe | Gly 10 | Ala | Thr | Val | Glu | Leu 15 | Leu |
|---|---|---|---|---|---|---|---|---|---|---|---|---|---|---|---|
| Ser | Phe | Leu | Pro 20 | Ser | Asp | Phe | Phe | Pro 25 | Ser | Val | Arg | Asp | Leu 30 | Leu | Asp |
| Thr | Ala | Ser 35 | Ala | Leu | Tyr | Arg | Glu 40 | Ala | Leu | Glu | Ser | Pro 45 | Glu | His | Cys |
| Ser | Pro 50 | His | His | Thr | Ala | Leu 55 | Arg | Gln | Ala | Ile | Leu 60 | Cys | Trp | Gly | Glu |
| Leu 65 | Met | Thr | Leu | Ala | Thr 70 | Trp | Val | Gly | Asn | Asn 75 | Leu | Glu | Asp | Pro | Ala 80 |
| Ser | Arg | Asp | Leu | Val 85 | Val | Asn | Tyr | Val | Asn 90 | Thr | Asn | Met | Gly | Leu 95 | Lys |
| Ile | Arg | Gln | Leu 100 | Leu | Trp | Phe | His | Ile 105 | Ser | Cys | Leu | Thr | Phe 110 | Gly | Arg |
| Glu | Thr | Val 115 | Leu | Glu | Tyr | Leu | Val 120 | Ser | Phe | Gly | Val | Trp 125 | Ile | Arg | Thr |
| Pro | Pro 130 | Ala | Tyr | Arg | Pro | Pro 135 | Asn | Ala | Pro | Ile | Leu 140 | Ser | Thr | Leu | Pro |
| Glu 145 | Thr | Thr | Val | Val | Arg 150 | Arg | Arg | Thr | Glu | Ala 155 | Gly | Pro | Leu | Glu | Glu 160 |
| Glu | Leu | Pro | Arg | Leu 165 | Ala | Asp | Ala | Asp | Leu 170 | Asn | Arg | Arg | Val | Ala 175 | Glu |
| Asp | Leu | Asn | Leu 180 | Gly | Asn | Leu | Asn | Val 185 | Arg | Ser | Phe | Arg | Gln 190 | Asn | Arg |
| Leu | Leu | Ser 195 | Ser | Lys | Ser | Arg | Thr 200 | Met | Ser | Asn | Leu | Val 205 | Leu | Arg | Leu |
| Arg | Gln 210 | Thr | Ile | Leu | Ser | | | | | | | | | | |

By only varying the number of bases (i.e., single nucleotides or base pairs referring to pairs of complementary nucleotides) between the ribosomal binding site and the start codon without the second codon change, an increase in expression is also obtainable. Preferably the spacing (i.e. spacer) between the ribosomal binding site and the start codon is between 8 and 20 nucleotides. Most preferably 10 to 15 nucleotides are between the ribosomal binding site and the start codon. Sequence ID No: 13 and Sequence ID No: 14 are good examples of a 10 base pair and 8 base pair spacer, respectively. The particular nucleotide composition chosen to vary the distance between the ribosomal binding site and the start codon can vary. Preferably the nucleotides are chosen to have a high degree of homology with the same region between the ribosomal binding sites and the start codons of the host organisms.

Although the particular modification of the present invention at the second codon utilizes GCT as the second codon, the particular modification of the second codon is not limited to only GCT. For example, any codon utilized by a large number of the host organisms can be engineered into the second codon region. Preferred E. coli codons in the second position are AAA, AGC, GCG, AAC, TCT, AAT, ACC, AGT, ACA, GCT, ACT, CAA, GCA, GAA, GGT and ATC. It is unexpected that varying the second codon alone results in increased expression. As evident from FIG. 1, changing the second codon results in a two-fold increase in expression over the native sequence.

Since the modification of the gene at the second codon is especially beneficial for enhancement and expression in the E. coli host, an E. coli host is preferred.

Although any single alteration of the invention (e.g., spacer between the ribosomal binding site and start codon, second codon change, and deletion of basepair 455 or 468) in the DNA molecule results in increased expression of about two (2) fold over the native sequence, if any two alterations are made in combination, about a ten (10) fold increase in expression is obtained. If all three alterations are made in combination, about a twenty-five (25) fold increase in expression is obtained. Importantly, the antigenicity of the HBcAg is not compromised by the alterations. Even the deletion of base pair 455 or 468, which creates a frame shift at the C-terminus of the HBcAg protein, does not alter the antigenicity of the protein.

Sequence ID No: 1 was originally amplified from an HBsAg positive plasma using appropriate primers and standard protocols. Now that the sequence is known, the HBcAg sequence can be prepared in a variety of ways and therefore is not limited to any particular preparation means.

For example, the nucleotide sequences of the invention can be prepared by use of recombinant DNA technology or, alternatively, by automated synthesis. The sequences of the invention can also be cloned in a suitable vector and amplified in a suitable host.

Also, sequences of the invention can be synthesized using commercially available methods and equipment. For example, the solid phase phosphotriester method can be used to produce the sequences of the invention. The sequences can be conveniently synthesized by the modified phosphotriester method using fully protected DNA building blocks. Such synthetic methods can be carried out in substantial accordance with the procedure of Itakura, et al., 1977, *Science* 198:1056 and Crea, et al., 1978, *Proc. Nat Acad. Sci. U.S.A.*, 75:575, and Narang, et al., 1980, *Methods in Enzymology*, 68:90. In addition to manual procedures the sequences can be synthesized using automated synthesizers.

Methods for solution and solid phase synthesis are widely known, and various commercially available automatic synthesizers can be used in accordance with known protocols. See, for example Stewart & Young, *Solid Phase Peptide Synthesis* 2d Edition, Pierce Chemical Company, 1984; Tam, et al., *J. Am. Chem. Assoc.* 105:6442 (1983) and Merrifield, et al., *Biochemistry* 21:5020 (1982), which are incorporated herein by reference. The sequences of the invention can be produced by a number of procedures, including synthetic DNA synthesis, cDNA cloning, genomic cloning, polymerase chain reaction (PCR) technology, or a combination or these approaches. See, e.g., Maniatis, *MOLECULAR CLONING, A LABORATORY MANUAL*, 1982. Mutagenesis procedures to produce "deletion mutants" that encode the desired sequence can also be employed. Procedures suitable for producing such mutants include polymerase chain reaction technology and variations thereof, or site specific mutagenesis procedures similar to those of Kunkel, *Proc. Natl. Acad. Sci. USA* 82:488 (1985) or Eckstein, et al., *Nucleic Acids Res.* 13:8764 (1985).

For cloning, a selected DNA sequence of the invention will be inserted into a suitable vector. A number of suitable vectors may be used, including cosmids, plasmids, bacteriophage and viruses. The principal requirements for such a vector are that it be capable of reproducing itself and stably transforming a host cell. Most preferably, the vector will comprise an "expression vector" which is capable of directing "expression" or cellular production of a peptide encoded by the DNA sequence of the invention. Typical expression vectors comprise a promoter region, a 5'-untranslated region, a coding sequence, a 3'-untranslated region, an origin of replication, a selective marker and a transcription termination site.

Suitable vectors for use in practicing the invention include pKK233-2 (Pharmacia), pKK223 2 (Pharmacia), pTTQ18 (Amersham, Arlington Heights, Ill.), pBTacl (Boehringer Mannheim), pET expression systems (Novagen, Madison, Wis.), and pPL-λ (Pharmacia).

Promoters for use in expression vectors include, lactose (lac) control elements, lambda ( PL) control elements, arabinose control elements, tryptophan (trp) control elements, and hybrids thereof. In addition, the vector may contain any one of a number of various markers facilitating selection of a transformed host cell. Such markers include genes associated with temperature sensitivity, drug resistance (e.g., resistance to ampicillin, chloramphenicol or tetracycline), or enzymes associated with visual characeristics of the host organism.

The vector may be prepared for insertion of the DNA sequence in a number of ways. Most simply, both the DNA sequence and the vector are digested with an appropriate set of restriction enzymes to generate sites suitable for ligation of the selected DNA sequence into the vector in an orientation and position suitable to allow expression of the peptide encoded by the sequence. Then, the DNA sequence is integrated into the vector by any of a number of suitable procedures, incuding treatment with a selected ligase.

After the sequence has been integrated into the vector, the vector may be used to transform a host cell. In general, the host cell may comprise any cellular organism including a prokaryotic cell or eukaryotic cell that is transformed with or competent of becoming transformed with the vector comprising the sequences of the present invention. Suitable host cells include, for example, bacterial cells such as *E. coli* or *B. subtilis*, mammalian cells (Kaufman, High Level Production of Proteins in Mammalian Cells, *Genetic Engineering Principles and Methods*, ed. J. K. Setlow Plenum Press, 9:155, 1988), yeast (Barr, et al., *Yeast Genetic Engineering*. eds. Butterworth, Boston, 1989), and insect cells (Maeda, Expression of Foreign Genes in Insects using Baculovius Vectors, T. E. Mittler eds. *Annual Review of Entomology* 34:351, 1989). A number of transformation techniques suitable for use with the particular vector-host cell combination may be employed. See, e.g., Maniatis, *Molecular Cloning, A Laboratory Manual,* Cold Spring Harbor Laboratories (1982).

For production of HBcAg product, the transformed host cell is cultured in a suitable medium under conditions designed to allow maximal expression with the particular combination of host and vector employed. By transforming hosts with sequences of the invention, greater amounts of HBcAg product is obtained.

Sequences of the invention can be used in methods and kits designed to detect the presence of antibodies in humans and therefore recognize Hepatitis B virus (HBV) infected humans and blood samples which have been infected by the hepatitis virus.

For example, the HBcAg produced by hosts transformed by recombinant DNA molecules of this invention or synthetically, can be used in the immunological diagnostic tests currently available for hepatitis B virus detection, such as radioimmunoassay or ELISA (enzyme linked immunosorbent assay). In one type of radioimmunoassay anti-core antigen antibody, raised in a laboratory animal, is attached to a solid phase, such as the inside of a test tube. HBcAg is then added to the tube so it can bind with the antibody. To the tube coated with the antigen-antibody complex is added a sample of the patient's serum, together with a known amount of HBV anti-core antibody labelled with a radioactive isotope such as radioactive iodine. Any HBV antibody in the patient's serum will compete with the labelled antibody for the free binding sites on the antigen-antibody complex. Once the serum has been allowed to interact, the excess liquid is removed, the test tube washed, and the amount of radioactivity measured. A positive result (i.e., that the patient's serum contains HBV antibody) is indicated by a low radioactive count. In one type of ELISA test, a microtitre plate is coated with HBcAg and a sample of a patient's serum is added. After a period of incubation permitting interaction of any antibody with the antigen, the plate is washed and a preparation of anti-human antibodies, raised in a laboratory animal, and which are linked to an enzyme label, is added, incubated to allow reaction to take place, and the plate rewashed. Thereafter, enzyme substrate is added to the microtitre plate and incubated for a period of time to allow the enzyme to work on the substrate, and the adsorbance of the final preparation is measured. A large change in adsorbance indicates a positive result.

The following examples illustrate the specific embodiments of the invention described in this document. As would be apparent to skilled artisans, various changes and modifications are possible and are contemplated within the scope of the invention described.

EXAMPLES

Materials and Preparation

Amplification of Core Gene

Polymerase chain reactions (PCR) are set up as follows:

| | |
|---|---|
| H₂O | 21.5 μl |
| PCR 10× Buffer* | 10.0 μl |
| 1.25 mM dNTPs | 16.0 μl |
| 20 μM Forward Primer | 1.0 μl |
| 20 μM Reverse Primer | 1.0 μl |
| HBV DNA | 50.0 μl |
| P/E Amplitaq | 0.5 μl |
| | 100.0 μl |

*PCR 10×. Buffer: 30 cycles: 95 degrees C. - 2.0 minutes
500 mM KCl 50 degrees C. - 1.5 minutes
100 mM Tris-HCl (pH 8.3) 72 degrees C. - 1.5 minutes
15 mM MgCl₂
0.1% gelatin

Oligonucleotide Primer Design and Synthesis

Oligonucleotide primers are synthesized on an Applied Biosystems, Inc. (ABI) DNA Synthesizer Model 381-A (Foster City, Calif.), or equivalent, according to manufacturer's specifications. "Trityl-On" oligonucleotides are purified using ABI "OPC" purification columns of equivalent according to manufacturer's protocol. One ml of eluent is dried in a Savant Speed-Vac, or equivalent, and resuspended in 100 μl of 10 mM Tris-HCl (pH 7.2), 1 mM EDTA. A 20 μM Stock solution of each primer is made for use in the PCR.

The following is the list of oligo primers for amplifying the core gene for cloning and expression.

| | | Forward primers for expression in pKK233 |
|---|---|---|
| "native" | (Seq ID No: 15) | GGCC ATG GAC ATT GAC CCT TAT AAA |
| 2nd codon | (Seq ID No: 16) | GGCC ATG <u>GTC</u> ATT GAC CCT TAT AAA GAA TTT GGA |
| | | Forward primers for expression in pKK223 |
| | | EcoRI |
| 10 bp spacer | (Seq ID No: 17) | CCGAATTC ATG GAC ATT GAC CCT TAT AAA |
| 2nd + 10 bp | (Seq ID No: 18) | CCGAATTC ATG <u>GTC</u> ATT GAC CCT TAT AAA |
| 11 bp | (Seq ID No: 19) | CGGAATTCG ATG GAC ATT GAC CCT TAT AAA |
| 12 bp | (Seq ID No: 20) | CGGAATTCGG ATG GAC ATT GAC CCT TAT AAA |
| 13 bp | (Seq ID No: 21) | CGGAATTCGGA ATG GAC ATT GAC CCT TAT AAA |
| 14 bp | (Seq ID No: 22) | CGGAATTCGGAT ATG GAC ATT GAC CCT TAT AAA |
| 15 bp | (Seq ID No: 23) | CGGGAATTCGGATC ATG GAC ATT GAC CCT TAT AAA |
| | | Reverse primer for both pKK233 and pKK223 |
| | | HindIII |
| | (Seq ID No: 24) | GGAAGCTT CTA ACA TTG AGA TTC CCG AGA TTG AGA TCT TCT GCG |

EXAMPLE 1

Isolation of Hepatitis B DNA

Using a protocol in substantial accordance with I. Baginski, et. al. "Detection of Hepatitis B Virus", In PCR Protocols, edited by M. A. Innis, D. H. Gelfand, J. J. Sninsky and T. J. White, 348-355, Academic Press, Inc. (1990). Hepatitis B virus (HBV) DNA is isolated from an HBsAg positive serum (sample #2791-19A obtained from Interstate Blood Bank, Inc., Memphis Tenn.) as follows:

To about 60 μl of HBsAg positive serum is added about 75 μl of 250 μg/ml proteinase K (Boehringer Mannheim, Indianapolis, Ind.) in: 0.25% SDS, 5mM EDTA, 10 mM Tris-HCl (pH 8.0). This solution is incubated for about 2 hours at about 56 degrees C. The proteinase K is then heat inactivated at about 95 degrees C. for about 10 minutes. The total volume is brought to 1215 μl in 1× Taq Polymerase buffer: 50 mM KCl, 10 mM Tris-HCl (pH 8.4), 2.5 mM $MgCl_2$, 0.01% gelatin (w/v), 0.5% Tween 20, 0.5% NP 40. Fifty microliters of this prepared DNA is used in subsequent polymerase chain reactions (PCRs) for generating HBcAg clones.

EXAMPLE 2

Cloning of Amplified HBcAg Gene Fragment

A PCR is set up using primers Sequence ID No: 15 and Sequence ID No: 24 to generate the first core gene fragment to be cloned. The resulting ~570 bp fragment and the expression vector pKK233-2 (Pharmacia) ar doubly digested with NcoI/HindIII (BRL). A ligation is set up with T4 ligase (BRL). Using a method in substantial accordance witin the teaching of D. H. Hanahan, "Techniques for Transformation of *E. coli*", In DNA cloning volume I, a practical approach, edited by D. M. Glover, 109, IRL Press Limited (1985), frozen competent *E. coli* strain XL1Blue (Stratagene) is transformed with the ligation, spreading 100 μl of the transformation mix on LB (100 μg/ml ampicillin) plates. Transformants are screened for inserts and those containing the desired fragment are used in expression experiments.

EXAMPLE 3

Expression of Core Protein

Cultures (12.5 ml) LB (100 μg/ml ampicillin) are grown to mid log then induced with isopropylthio-β-D-galactoside (IPTG) to a final concentration of 1 mM. Cultures are allowed to grow overnight, approximately 16 hours. 1.5 ml of the culture is removed, spun down at full speed in a Brinkman microfuge or equivalent. The pellet is resuspended in 100 μl 1× sample prep buffer (U. K. Laemmli, Nature 227:680 (1970), boiled about 5 minutes and 10 μl run on a 12% SDS PAGE gel at 40 mA for about 1¼ hour. A Western blot is prepared by transferring proteins from the gel to Immobilon-P membrane (Millipore, Bedford, Mass.), or equivalent at 100 mA in a Hoefer Semidry Transfer apparatus or equivalent for 1 hour using Towbin buffer (25 mM Tris (pH8.3), 192 mM Glycine, 15% methanol). After transfer, membrane is blocked with 5% BSA in 1× Tris buffered saline (TBS) (10mM Tris-HCl, (pH 8.0), 0.9% NaCl) for 30 minutes. An anti HBcAg polyclonal antibody (this antibody solution in phosphate buffered saline (PBS)+a carrier protein, is a component of a kit, but is sold separately, this antibody concentration is unknown)(BioGenex Laboratories, Dublin, Calif. - catalog #PA082-5P) is incubated with the membrane for 1 hour. Membrane is washed 5× with TBS. Membrane was then incubated with a goat anti-rabbit horseradish peroxidase conjugated polyclonal antibody (Cappel Organonteknika, West Chester, Pa.) at 1:1000 in the 5% bovine serum albumin (BSA)/TBS solution for one hour. Membrane is washed 5× with TBS then developed with 4-chloro-1-naphthol and hydrogen peroxide. Clones expressing HBcAg show the appropriate size reactive band at ~21 KDa. However, all show very low levels of expression.

EXAMPLE 4

Increasing Expression Levels

Oliqonucleotide primers are synthesized (see "Materials and Preparations" above) to allow about 10 to 15 bp between the ribosome binding site and the ATG start codon. PCRs are set up with the following primer sets using the method previously described: Sequence ID No: 17 - Sequence ID No: 24, Sequence ID No: 19 - Sequence ID No: 24, Sequence ID No: 20 - Sequence ID No: 24, Sequence ID No: 21 - Sequence ID No: 24, Sequence ID No: 22 - Sequence ID No: 24, and Sequence ID No: 23 - Sequence ID No: 24. All PCRs generate the appropriate ~570 bp fragment. These fragments are doubly digested with EcoRI and Hind III and directionally cloned into pKK223-3 (Pharmacia, Piscataway, N.J.) as described above. Transformations are set up as previously described.

LB plates are spread with 50 μl of 1M IPTG and a membrane sandwich placed on the surface of the agar. The sandwich is prepared by placing a nitrocellulose membrane (BA 85; Schleicher & Schuell, Inc., Keene, N.H.) or equivalent, on top of the agar medium and then a cellulose acetate membrane (OE67; Schleicher & Schuell), or equivalent, on top of that. Transformations are then plated as before and plates incubated at about 37 degrees C. overnight. The nitrocellulose filters are removed and blocked for about 1 hour in 5% BSA/TBS. An anti-HBcAg monoclonal antibody is added at 20 μg/ml and incubated for about 1 hour. Membranes are washed with TBS a secondary goat anti-mouse horseradish conjugated antibody (Cappel) is added at 1:2000 in 5% BSA/TBS for about 1 hour. Membranes are washed with TBS and developed with 4-chloro-1-naphthol and hydrogen peroxide. Reactive colonies are patched out for a second direct colony immunoblot (DCI) and again chosen for reactivity. The 10 bp spacer clones are chosen for further analysis and quantitation in a sandwich ELISA.

Two oligo primers Sequence ID No: 16 and Sequence ID No: 18 (see "materials and Preparation",) are designed to change the HBcAg second codon from GAC to GCT. Primer Sequence ID No: 16 changes the second codon with the fragment to be cloned into pKK233-2 while primer Sequence ID No: 18 allows for the 10 bp spacer as well as the second codon change. PCRs are set up and fragments cloned as previously mentioned. DCI are set up for screening transformants. Reactive colonies are chosen for further analysis and quantitation in a sandwich ELISA.

EXAMPLE 5

Quantitation for Increased Expression of HBcAg Strains Tested by ELISA

| Strain | Vector | Fragment |
|---|---|---|
| Sequence ID No: 1 | pKK233-2 | HBcAg DNA sequence |
| Sequence ID No: 3 | pKK233-3 | 10 bp spacer |
| Sequence ID No: 5 | Pkk223-3 | 10 bp spacer + 2nd codon change |
| Control | pKK223-3 | No insert |

3 ml overnight cultures LB - 100 μg/ml Ampicillin) of each of the above stains are grown at about 37 degrees C. 250 μl of the overnight culture (1:50) is used to inoculate 12.5 ml cultures (same medium). Cultures are grown to 0.6-0.8 $A_{600}$ then induced by adding 1M IPTG to ~1 mM. Cultures are allowed to grow overnight (about 19 hours). One O.D. unit ($A_{600}$) of cells from each culture is removed and spun down and resuspended in 975 ul of PBS to which 10 μl of 10 μg/ml lysozyme (Sigma, St. Louis, Mo.) in PBS was added. Each is frozen in liquid nitrogen and thawed at about 37 degrees C. 3 times. 1M $MgCl_2$ is added to 5 mM (5 μl) and 10 μl of 1 mg/ml DNase (Sigma) is added and then the solution is incubated at room temperature for about 10 minutes. Lysates are spun at ~7000 xg in microfuge for about 10 minutes. The supernatant fraction is removed and used in the ELISA.

One hundred microliters of "capture" antibody is coated onto plates at 20 μg/ml in phosphate buffered saline (PBS) (10 mM Phosphate (pH 7.2), 130 mM NaCl) at about 4 degrees C. overnight. Capture antibody solution is removed and the wells blocked with 2.5% BSA in PBS for about 1 hour. Fifty microliters of serial two fold dilutions of *E. coli* lysates (in 2.5% BSA/PBS) from 1:8 down to 1:16,000 are placed in wells and incubated for about 1 hour. Wells are washed 5 times with PBS+0.05% Tween 20 (PBS-Tween). Fifty microliters of biotinylated detector antibody is added at 5 μg/ml in 2.5% BSA/PBS to each well and incubated for about 1 hour. Plates are washed 5 times with PBS-Tween. Fifty microliters of Avidin-HRP (1 mg/ml) (Sigma) diluted 1:2000 in 2.5% BSA/PBS are added to each well and incubated for about 1 hour. Plates are washed 5 times with PBS-Tween, and developed with 50 μl of o-phenylenediamine dihydrochloride (OPD) (20 mg OPD, 100 mM citrate (pH 5.5), 7 μl 30% hydrogen peroxide). After two minutes the reaction is stopped by adding about 50 μl of 4.5M sulphuric acid. Plates are read at $A_{490}$. Relative quantities of HBcAg in each lysate is calculated against a standard curve generated with purified HBcAg from 20 μg to 0.02 ng per well (2 fold serial dilution).

Although the invention has been described with respect to specific modifications, the details thereof are not to be construed as limitations, for it will be apparent that various equivalents, changes and modifications may be resorted to without departing from the spirit and scope thereof, and it is understood that such equivalent embodiments are to be included therein.

---

( 1 ) GENERAL INFORMATION:

( i i i ) NUMBER OF SEQUENCES: 24

( v i ) CURRENT APPLICATION DATA:
      ( A ) APPLICATION NUMBER:
      ( B ) FILING DATE:

( 2 ) INFORMATION FOR SEQ ID NO:1:

( i ) SEQUENCE CHARACTERISTICS:
      ( A ) LENGTH: 558 base pairs
      ( B ) TYPE: nucleic acid
      ( C ) STRANDEDNESS: double
      ( D ) TOPOLOGY: linear ( i x ) FEATURE:
      ( A ) NAME/KEY: CDS
      ( B ) LOCATION: 1..558

( x i ) SEQUENCE DESCRIPTION: SEQ ID NO:1:

```
ATG  GAC  ATT  GAC  CCT  TAT  AAA  GAA  TTT  GGA  GCT  ACT  GTG  GAG  TTA  CTC         48
Met  Asp  Ile  Asp  Pro  Tyr  Lys  Glu  Phe  Gly  Ala  Thr  Val  Glu  Leu  Leu
 1                     5                    10                    15

TCG  TTT  TTG  CCT  TCT  GAC  TTC  TTT  CCT  TCC  GTC  AGA  GAT  CTC  CTA  GAC         96
Ser  Phe  Leu  Pro  Ser  Asp  Phe  Phe  Pro  Ser  Val  Arg  Asp  Leu  Leu  Asp
                      20                    25                    30

ACC  GCC  TCA  GCT  CTG  TAT  CGG  GAA  GCC  TTA  GAG  TCT  CCT  GAG  CAT  TGC        144
Thr  Ala  Ser  Ala  Leu  Tyr  Arg  Glu  Ala  Leu  Glu  Ser  Pro  Glu  His  Cys
           35                    40                    45

TCA  CCT  CAC  CAT  ACC  GCA  CTC  AGG  CAA  GCC  ATT  CTC  TGC  TGG  GGG  GAA        192
Ser  Pro  His  His  Thr  Ala  Leu  Arg  Gln  Ala  Ile  Leu  Cys  Trp  Gly  Glu
      50                    55                     60

TTG  ATG  ACT  CTA  GCT  ACC  TGG  GTG  GGT  AAT  AAT  TTG  GAA  GAT  CCA  GCA        240
Leu  Met  Thr  Leu  Ala  Thr  Trp  Val  Gly  Asn  Asn  Leu  Glu  Asp  Pro  Ala
 65                    70                    75                          80

TCA  AGG  GAC  CTA  GTA  GTC  AAT  TAT  GTT  AAT  ACT  AAC  ATG  GGT  TTA  AAA        288
Ser  Arg  Asp  Leu  Val  Val  Asn  Tyr  Val  Asn  Thr  Asn  Met  Gly  Leu  Lys
                      85                    90                     95
```

```
ATT  AGG  CAA  CTA  TTG  TGG  TTT  CAT  ATA  TCT  TGC  CTT  ACT  TTT  GGA  AGA        336
Ile  Arg  Gln  Leu  Leu  Trp  Phe  His  Ile  Ser  Cys  Leu  Thr  Phe  Gly  Arg
          100                          105                         110

GAG  ACT  GTA  CTT  GAA  TAT  TTG  GTC  TCT  TTC  GGA  GTG  TGG  ATT  CGC  ACT        384
Glu  Thr  Val  Leu  Glu  Tyr  Leu  Val  Ser  Phe  Gly  Val  Trp  Ile  Arg  Thr
          115                          120                         125

CCT  CCA  GCC  TAT  AGA  CCA  CCA  AAT  GCC  CCT  ATC  TTA  TCA  ACA  CTT  CCG        432
Pro  Pro  Ala  Tyr  Arg  Pro  Pro  Asn  Ala  Pro  Ile  Leu  Ser  Thr  Leu  Pro
          130                          135                         140

GAA  ACT  ACT  GTT  GTT  AGA  CGA  CGG  GAC  CGA  GGC  AGG  TCC  CCT  AGA  AGA        480
Glu  Thr  Thr  Val  Val  Arg  Arg  Arg  Asp  Arg  Gly  Arg  Ser  Pro  Arg  Arg
145                      150                      155                     160

AGA  ACT  CCC  TCG  CCT  CGC  AGA  CGC  AGA  TCT  CAA  TCG  CCG  CGT  CGC  AGA        528
Arg  Thr  Pro  Ser  Pro  Arg  Arg  Arg  Arg  Ser  Gln  Ser  Pro  Arg  Arg  Arg
               165                          170                        175

AGA  TCT  CAA  TCT  CGG  GAA  TCT  CAA  TGT  TAG                                      558
Arg  Ser  Gln  Ser  Arg  Glu  Ser  Gln  Cys
          180                          185
```

( 2 ) INFORMATION FOR SEQ ID NO:2:

( i ) SEQUENCE CHARACTERISTICS:
    ( A ) LENGTH: 185 amino acids
    ( B ) TYPE: amino acid
    ( D ) TOPOLOGY: linear ( x i ) SEQUENCE DESCRIPTION: SEQ ID NO:2:

```
Met  Asp  Ile  Asp  Pro  Tyr  Lys  Glu  Phe  Gly  Ala  Thr  Val  Glu  Leu  Leu
 1                    5                    10                        15

Ser  Phe  Leu  Pro  Ser  Asp  Phe  Phe  Pro  Ser  Val  Arg  Asp  Leu  Leu  Asp
          20                          25                         30

Thr  Ala  Ser  Ala  Leu  Tyr  Arg  Glu  Ala  Leu  Glu  Ser  Pro  Glu  His  Cys
          35                          40                         45

Ser  Pro  His  His  Thr  Ala  Leu  Arg  Gln  Ala  Ile  Leu  Cys  Trp  Gly  Glu
          50                          55                         60

Leu  Met  Thr  Leu  Ala  Thr  Trp  Val  Gly  Asn  Asn  Leu  Glu  Asp  Pro  Ala
65                        70                       75                        80

Ser  Arg  Asp  Leu  Val  Val  Asn  Tyr  Val  Asn  Thr  Asn  Met  Gly  Leu  Lys
               85                          90                            95

Ile  Arg  Gln  Leu  Leu  Trp  Phe  His  Ile  Ser  Cys  Leu  Thr  Phe  Gly  Arg
          100                         105                        110

Glu  Thr  Val  Leu  Glu  Tyr  Leu  Val  Ser  Phe  Gly  Val  Trp  Ile  Arg  Thr
          115                         120                        125

Pro  Pro  Ala  Tyr  Arg  Pro  Pro  Asn  Ala  Pro  Ile  Leu  Ser  Thr  Leu  Pro
          130                         135                        140

Glu  Thr  Thr  Val  Val  Arg  Arg  Arg  Asp  Arg  Gly  Arg  Ser  Pro  Arg  Arg
145                     150                      155                       160

Arg  Thr  Pro  Ser  Pro  Arg  Arg  Arg  Arg  Ser  Gln  Ser  Pro  Arg  Arg  Arg
               165                         170                          175

Arg  Ser  Gln  Ser  Arg  Glu  Ser  Gln  Cys
          180                         185
```

( 2 ) INFORMATION FOR SEQ ID NO:3:

( i ) SEQUENCE CHARACTERISTICS:
    ( A ) LENGTH: 558 base pairs
    ( B ) TYPE: nucleic acid
    ( C ) STRANDEDNESS: double
    ( D ) TOPOLOGY: linear ( i x ) FEATURE:
    ( A ) NAME/KEY: CDS
    ( B ) LOCATION: 1..558

( x i ) SEQUENCE DESCRIPTION: SEQ ID NO:3:

```
ATG GAC ATT GAC CCT TAT AAA GAA TTT GGA GCT ACT GTA GAG TTA CTC      48
Met Asp Ile Asp Pro Tyr Lys Glu Phe Gly Ala Thr Val Glu Leu Leu
 1               5                  10                  15

TCG TTT TTG CCT TCT GAC TTC TTT CCT TCC GTC AGA GAT CTC CTA GAC      96
Ser Phe Leu Pro Ser Asp Phe Phe Pro Ser Val Arg Asp Leu Leu Asp
                20                  25                  30

ACC GCC TCA GCT CTG TAT CGG GAA GCC TTA GAG TCT CCT GAG CAT TGC     144
Thr Ala Ser Ala Leu Tyr Arg Glu Ala Leu Glu Ser Pro Glu His Cys
         35                  40                  45

TCA CCT CAC CAT ACC GCA CTC AGG CAA GCC ATT CTC TGC TGG GGG GAA     192
Ser Pro His His Thr Ala Leu Arg Gln Ala Ile Leu Cys Trp Gly Glu
     50                  55                  60

TTG ATG ACT CTA GCT ACC TGG GTG GGT AAT AAT TTG GAA GAT CCA GCA     240
Leu Met Thr Leu Ala Thr Trp Val Gly Asn Asn Leu Glu Asp Pro Ala
 65                  70                  75                  80

TCA AGG GAT CTA GTA GTC AAT TAT GTT AAT ACT AAC ATG GGT TTA AAA     288
Ser Arg Asp Leu Val Val Asn Tyr Val Asn Thr Asn Met Gly Leu Lys
                 85                  90                  95

ATT AGG CAA CTA TTG TGG TTT CAT ATA TCT TGC CTT ACT TTT GGA AGA     336
Ile Arg Gln Leu Leu Trp Phe His Ile Ser Cys Leu Thr Phe Gly Arg
                100                 105                 110

GAG ACT GTA CTT GAA TAT TTG GCC TCT TTC GGA GTG TGG ATT CGC ACT     384
Glu Thr Val Leu Glu Tyr Leu Ala Ser Phe Gly Val Trp Ile Arg Thr
        115                 120                 125

CCT CCA GCC TAT AGA CCA CCA AAT GCC CCT ATC TTA TCA ACA CTT CCG     432
Pro Pro Ala Tyr Arg Pro Pro Asn Ala Pro Ile Leu Ser Thr Leu Pro
    130                 135                 140

GAA ACT ACT GTT GTT AGA CGA CGG GAC CGA GGC AGG TCC CCT AGA AGA     480
Glu Thr Thr Val Val Arg Arg Arg Asp Arg Gly Arg Ser Pro Arg Arg
145                 150                 155                 160

AGA ACT CCC TCG CCT CGC AGA CGC AGA TCT CAA TCG CCG CGT CGC AGA     528
Arg Thr Pro Ser Pro Arg Arg Arg Arg Ser Gln Ser Pro Arg Arg Arg
                165                 170                 175

AGA TCT CAA TCT CGG GAA TCT CAA TGT TAG                             558
Arg Ser Gln Ser Arg Glu Ser Gln Cys
                180                 185
```

( 2 ) INFORMATION FOR SEQ ID NO:4:

( i ) SEQUENCE CHARACTERISTICS:
        ( A ) LENGTH: 185 amino acids
        ( B ) TYPE: amino acid
        ( D ) TOPOLOGY: linear ( x i ) SEQUENCE DESCRIPTION: SEQ ID NO:4:

```
Met Asp Ile Asp Pro Tyr Lys Glu Phe Gly Ala Thr Val Glu Leu Leu
 1               5                  10                  15

Ser Phe Leu Pro Ser Asp Phe Phe Pro Ser Val Arg Asp Leu Leu Asp
                20                  25                  30

Thr Ala Ser Ala Leu Tyr Arg Glu Ala Leu Glu Ser Pro Glu His Cys
         35                  40                  45

Ser Pro His His Thr Ala Leu Arg Gln Ala Ile Leu Cys Trp Gly Glu
     50                  55                  60

Leu Met Thr Leu Ala Thr Trp Val Gly Asn Asn Leu Glu Asp Pro Ala
 65                  70                  75                  80
```

```
Ser  Arg  Asp  Leu  Val  Val  Asn  Tyr  Val  Asn  Thr  Asn  Met  Gly  Leu  Lys
               85                  90                       95

Ile  Arg  Gln  Leu  Leu  Trp  Phe  His  Ile  Ser  Cys  Leu  Thr  Phe  Gly  Arg
               100                 105                      110

Glu  Thr  Val  Leu  Glu  Tyr  Leu  Ala  Ser  Phe  Gly  Val  Trp  Ile  Arg  Thr
          115                      120                      125

Pro  Pro  Ala  Tyr  Arg  Pro  Pro  Asn  Ala  Pro  Ile  Leu  Ser  Thr  Leu  Pro
          130                 135                      140

Glu  Thr  Thr  Val  Val  Arg  Arg  Arg  Asp  Arg  Gly  Arg  Ser  Pro  Arg  Arg
145                      150                 155                           160

Arg  Thr  Pro  Ser  Pro  Arg  Arg  Arg  Arg  Ser  Gln  Ser  Pro  Arg  Arg  Arg
                    165                      170                      175

Arg  Ser  Gln  Ser  Arg  Glu  Ser  Gln  Cys
               180                 185
```

(2) INFORMATION FOR SEQ ID NO:5:

(i) SEQUENCE CHARACTERISTICS:
      (A) LENGTH: 645 base pairs
      (B) TYPE: nucleic acid
      (C) STRANDEDNESS: double
      (D) TOPOLOGY: linear (ix) FEATURE:
      (A) NAME/KEY: CDS
      (B) LOCATION: 1..645

(xi) SEQUENCE DESCRIPTION: SEQ ID NO:5:

```
ATG  GCT  ATT  GAC  CCT  TAT  AAA  GAA  TTT  GGA  GCT  ACT  GTG  GAG  TTA  CTC    48
Met  Ala  Ile  Asp  Pro  Tyr  Lys  Glu  Phe  Gly  Ala  Thr  Val  Glu  Leu  Leu
1                   5                   10                      15

TCG  TTT  TTG  CCT  TCT  GAC  TTC  TTT  CCT  TCC  GTC  AGA  GAT  CTC  CTA  GAC    96
Ser  Phe  Leu  Pro  Ser  Asp  Phe  Phe  Pro  Ser  Val  Arg  Asp  Leu  Leu  Asp
               20                  25                      30

ACC  GCC  TCA  GCT  CTG  TAT  CGG  GAA  GCC  TTA  GAG  TCT  CCT  GAG  CAT  TGC   144
Thr  Ala  Ser  Ala  Leu  Tyr  Arg  Glu  Ala  Leu  Glu  Ser  Pro  Glu  His  Cys
          35                       40                        45

TCA  CCT  CAC  CAT  ACC  GCA  CTC  AGG  CAA  GCC  ATT  CTC  TCG  TGG  GGG  GAA   192
Ser  Pro  His  His  Thr  Ala  Leu  Arg  Gln  Ala  Ile  Leu  Ser  Trp  Gly  Glu
     50                       55                       60

TTG  ATG  ACT  CTA  GCT  ACC  TGG  GTG  GGT  AAT  AAT  TTG  GAA  GAT  CCA  GCA   240
Leu  Met  Thr  Leu  Ala  Thr  Trp  Val  Gly  Asn  Asn  Leu  Glu  Asp  Pro  Ala
65                       70                       75                        80

TCA  AGG  GAC  CTA  GTA  GTC  AAT  TAT  GTT  AAT  ACT  AAC  ATG  GGT  TTA  AAA   288
Ser  Arg  Asp  Leu  Val  Val  Asn  Tyr  Val  Asn  Thr  Asn  Met  Gly  Leu  Lys
               85                       90                       95

ATT  AGG  CAA  CTA  TTG  TGG  TTT  CAT  ATA  TCT  TGC  CTT  ACT  TTT  GGA  AGA   336
Ile  Arg  Gln  Leu  Leu  Trp  Phe  His  Ile  Ser  Cys  Leu  Thr  Phe  Gly  Arg
               100                      105                      110

GAG  ACT  GTA  CTT  GAA  TAT  TTG  GTC  TCT  TTC  GGA  GTG  TGG  ATT  CGC  ACT   384
Glu  Thr  Val  Leu  Glu  Tyr  Leu  Val  Ser  Phe  Gly  Val  Trp  Ile  Arg  Thr
          115                      120                      125

CCT  CCA  GCC  TAT  AGA  CCA  CCA  AAT  GCC  CCT  ATC  TTA  TCA  ACA  CTT  CCG   432
Pro  Pro  Ala  Tyr  Arg  Pro  Pro  Asn  Ala  Pro  Ile  Leu  Ser  Thr  Leu  Pro
          130                      135                      140

GAA  ACT  ACT  GTT  GTT  AGA  CGA  CGG  GAC  CGA  GGC  AAT  CCC  CTA  GAA  GAA   480
Glu  Thr  Thr  Val  Val  Arg  Arg  Arg  Asp  Arg  Gly  Asn  Pro  Leu  Glu  Glu
145                      150                      155                      160

GAA  CTC  CCT  CGC  CTC  GCA  GAC  GCA  GAT  CTC  AAT  CGC  CGC  GTC  GCA  GAA   528
```

-continued

| | | | | Glu | Leu | Pro | Arg | Leu | Ala | Asp | Ala | Asp | Leu | Asn | Arg | Arg | Val | Ala | Glu | |
| | | | | | | | | 165 | | | | | 170 | | | | | 175 | | |

| GAT | CTC | AAT | CTC | GGG | AAT | CTC | AAT | GTT | AGA | AGC | TTC | CGA | CAA | AAC | CGC | 576 |
| Asp | Leu | Asn | Leu | Gly | Asn | Leu | Asn | Val | Arg | Ser | Phe | Arg | Gln | Asn | Arg | |
| | | | 180 | | | | | 185 | | | | | 190 | | | |

| CTA | CTC | TCT | TCT | AAA | AGT | CGG | ACT | ATG | TCT | AAT | TTA | GTC | TTG | CGT | CTT | 624 |
| Leu | Leu | Ser | Ser | Lys | Ser | Arg | Thr | Met | Ser | Asn | Leu | Val | Leu | Arg | Leu | |
| | | 195 | | | | | 200 | | | | | 205 | | | | |

| CGC | CAG | ACT | ATT | TTG | TCT | TAA | 645 |
| Arg | Gln | Thr | Ile | Leu | Ser | | |
| | | 210 | | | 215 | | |

( 2 ) INFORMATION FOR SEQ ID NO:6:

( i ) SEQUENCE CHARACTERISTICS:
        ( A ) LENGTH: 214 amino acids
        ( B ) TYPE: amino acid
        ( D ) TOPOLOGY: linear ( x i ) SEQUENCE DESCRIPTION: SEQ ID NO:6:

| Met | Ala | Ile | Asp | Pro | Tyr | Lys | Glu | Phe | Gly | Ala | Thr | Val | Glu | Leu | Leu |
| 1 | | | | 5 | | | | | 10 | | | | | 15 | |

| Ser | Phe | Leu | Pro | Ser | Asp | Phe | Phe | Pro | Ser | Val | Arg | Asp | Leu | Leu | Asp |
| | | | 20 | | | | | 25 | | | | | 30 | | |

| Thr | Ala | Ser | Ala | Leu | Tyr | Arg | Glu | Ala | Leu | Glu | Ser | Pro | Glu | His | Cys |
| | | | 35 | | | | | 40 | | | | | 45 | | |

| Ser | Pro | His | His | Thr | Ala | Leu | Arg | Gln | Ala | Ile | Leu | Ser | Trp | Gly | Glu |
| | | 50 | | | | | 55 | | | | | 60 | | | |

| Leu | Met | Thr | Leu | Ala | Thr | Trp | Val | Gly | Asn | Asn | Leu | Glu | Asp | Pro | Ala |
| 65 | | | | | 70 | | | | 75 | | | | | | 80 |

| Ser | Arg | Asp | Leu | Val | Val | Asn | Tyr | Val | Asn | Thr | Asn | Met | Gly | Leu | Lys |
| | | | | 85 | | | | | 90 | | | | | 95 | |

| Ile | Arg | Gln | Leu | Leu | Trp | Phe | His | Ile | Ser | Cys | Leu | Thr | Phe | Gly | Arg |
| | | | 100 | | | | | 105 | | | | | 110 | | |

| Glu | Thr | Val | Leu | Glu | Tyr | Leu | Val | Ser | Phe | Gly | Val | Trp | Ile | Arg | Thr |
| | | 115 | | | | | 120 | | | | | 125 | | | |

| Pro | Pro | Ala | Tyr | Arg | Pro | Pro | Asn | Ala | Pro | Ile | Leu | Ser | Thr | Leu | Pro |
| | 130 | | | | | 135 | | | | | 140 | | | | |

| Glu | Thr | Thr | Val | Val | Arg | Arg | Arg | Asp | Arg | Gly | Asn | Pro | Leu | Glu | Glu |
| 145 | | | | | 150 | | | | 155 | | | | | | 160 |

| Glu | Leu | Pro | Arg | Leu | Ala | Asp | Ala | Asp | Leu | Asn | Arg | Arg | Val | Ala | Glu |
| | | | | 165 | | | | | 170 | | | | | 175 | |

| Asp | Leu | Asn | Leu | Gly | Asn | Leu | Asn | Val | Arg | Ser | Phe | Arg | Gln | Asn | Arg |
| | | | 180 | | | | | 185 | | | | | 190 | | |

| Leu | Leu | Ser | Ser | Lys | Ser | Arg | Thr | Met | Ser | Asn | Leu | Val | Leu | Arg | Leu |
| | | 195 | | | | | 200 | | | | | 205 | | | |

| Arg | Gln | Thr | Ile | Leu | Ser |
| | | 210 | | | |

( 2 ) INFORMATION FOR SEQ ID NO:7:

( i ) SEQUENCE CHARACTERISTICS:
        ( A ) LENGTH: 558 base pairs
        ( B ) TYPE: nucleic acid
        ( C ) STRANDEDNESS: double
        ( D ) TOPOLOGY: linear ( i x ) FEATURE:

(A) NAME/KEY: CDS
(B) LOCATION: 1..558

(xi) SEQUENCE DESCRIPTION: SEQ ID NO:7:

| | | | | | | | | | | | | | | | | |
|---|---|---|---|---|---|---|---|---|---|---|---|---|---|---|---|---|
| ATG | GCT | ATT | GAC | CCT | TAT | AAA | GAA | TTT | GGA | GCT | ACT | GTG | GAG | TTA | CTC | 48 |
| Met | Ala | Ile | Asp | Pro | Tyr | Lys | Glu | Phe | Gly | Ala | Thr | Val | Glu | Leu | Leu | |
| 1 | | | | 5 | | | | | 10 | | | | | 15 | | |
| TCG | TTT | TTG | CCT | TCT | GAC | TTC | TTT | CCT | TCC | GTC | AGA | GAT | CTC | CTA | GAC | 96 |
| Ser | Phe | Leu | Pro | Ser | Asp | Phe | Phe | Pro | Ser | Val | Arg | Asp | Leu | Leu | Asp | |
| | | | 20 | | | | | 25 | | | | 30 | | | | |
| ACC | GCC | TCA | GCT | CTG | TAT | CGG | GAA | GCC | TTA | GAG | TCT | CCT | GAG | CAT | TGC | 144 |
| Thr | Ala | Ser | Ala | Leu | Tyr | Arg | Glu | Ala | Leu | Glu | Ser | Pro | Glu | His | Cys | |
| | | 35 | | | | 40 | | | | | 45 | | | | | |
| TCA | CCT | CAC | CAT | ACC | GCA | CTC | AGG | CAA | GCC | ATT | CTC | TGC | TGG | GGG | GAA | 192 |
| Ser | Pro | His | His | Thr | Ala | Leu | Arg | Gln | Ala | Ile | Leu | Cys | Trp | Gly | Glu | |
| | 50 | | | | 55 | | | | | 60 | | | | | | |
| TTG | ATG | ACT | CTA | GCT | ACC | TGG | GTG | GGT | AAT | AAT | TTG | GAA | GAT | CCA | GCA | 240 |
| Leu | Met | Thr | Leu | Ala | Thr | Trp | Val | Gly | Asn | Asn | Leu | Glu | Asp | Pro | Ala | |
| 65 | | | | 70 | | | | | 75 | | | | | 80 | | |
| TCA | AGG | GAC | CTA | GTA | GTC | AAT | TAT | GGT | AAT | ACT | AAC | ATG | GGT | TTA | AAA | 288 |
| Ser | Arg | Asp | Leu | Val | Val | Asn | Tyr | Gly | Asn | Thr | Asn | Met | Gly | Leu | Lys | |
| | | | 85 | | | | | 90 | | | | | 95 | | | |
| ATT | AGG | CAA | CTA | TTG | TGG | TTT | CAT | ATA | TCT | TGC | CTT | ACT | TTT | GGA | AGA | 336 |
| Ile | Arg | Gln | Leu | Leu | Trp | Phe | His | Ile | Ser | Cys | Leu | Thr | Phe | Gly | Arg | |
| | | 100 | | | | 105 | | | | | 110 | | | | | |
| GAG | ACT | GTA | CTT | GAA | TAT | TTG | GTC | TCT | TTC | GGA | GTG | TGG | ATT | CGC | ACT | 384 |
| Glu | Thr | Val | Leu | Glu | Tyr | Leu | Val | Ser | Phe | Gly | Val | Trp | Ile | Arg | Thr | |
| | | 115 | | | | | 120 | | | | | 125 | | | | |
| CCT | CCA | GCC | TAT | AGA | CCA | CCA | AAT | GCC | CCT | ATC | TTA | TCA | ACA | CTT | CCG | 432 |
| Pro | Pro | Ala | Tyr | Arg | Pro | Pro | Asn | Ala | Pro | Ile | Leu | Ser | Thr | Leu | Pro | |
| | 130 | | | | | 135 | | | | | 140 | | | | | |
| GAA | ACT | ACT | GTT | GTT | AGA | CGA | CGG | GAC | CGA | GGC | AGG | TCC | CCT | AGA | AGA | 480 |
| Glu | Thr | Thr | Val | Val | Arg | Arg | Arg | Asp | Arg | Gly | Arg | Ser | Pro | Arg | Arg | |
| 145 | | | | | 150 | | | | | 155 | | | | | 160 | |
| AGA | ACT | CCC | TCG | CCT | CGC | AGA | CGC | AGA | TCT | CAA | TCG | CCG | CGT | CGC | AGA | 528 |
| Arg | Thr | Pro | Ser | Pro | Arg | Arg | Arg | Arg | Ser | Gln | Ser | Pro | Arg | Arg | Arg | |
| | | | | 165 | | | | | 170 | | | | | 175 | | |
| AGA | TCT | CAA | TCT | CGG | GAA | TCT | CAA | TGT | TAG | | | | | | | 558 |
| Arg | Ser | Gln | Ser | Arg | Glu | Ser | Gln | Cys | | | | | | | | |
| | | | 180 | | | | | 185 | | | | | | | | |

(2) INFORMATION FOR SEQ ID NO:8:

(i) SEQUENCE CHARACTERISTICS:
      (A) LENGTH: 185 amino acids
      (B) TYPE: amino acid
      (D) TOPOLOGY: linear (xi) SEQUENCE DESCRIPTION: SEQ ID NO:8:

| | | | | | | | | | | | | | | | |
|---|---|---|---|---|---|---|---|---|---|---|---|---|---|---|---|
| Met | Ala | Ile | Asp | Pro | Tyr | Lys | Glu | Phe | Gly | Ala | Thr | Val | Glu | Leu | Leu |
| 1 | | | | 5 | | | | | 10 | | | | | 15 | |
| Ser | Phe | Leu | Pro | Ser | Asp | Phe | Phe | Pro | Ser | Val | Arg | Asp | Leu | Leu | Asp |
| | | | 20 | | | | | 25 | | | | 30 | | | |
| Thr | Ala | Ser | Ala | Leu | Tyr | Arg | Glu | Ala | Leu | Glu | Ser | Pro | Glu | His | Cys |
| | | 35 | | | | 40 | | | | | 45 | | | | |
| Ser | Pro | His | His | Thr | Ala | Leu | Arg | Gln | Ala | Ile | Leu | Cys | Trp | Gly | Glu |
| | 50 | | | | 55 | | | | | 60 | | | | | |
| Leu | Met | Thr | Leu | Ala | Thr | Trp | Val | Gly | Asn | Asn | Leu | Glu | Asp | Pro | Ala |
| 65 | | | | 70 | | | | | 75 | | | | | 80 | |
| Ser | Arg | Asp | Leu | Val | Val | Asn | Tyr | Gly | Asn | Thr | Asn | Met | Gly | Leu | Lys |
| | | | 85 | | | | | 90 | | | | | 95 | | |

| Ile | Arg | Gln | Leu | Leu | Trp | Phe | His | Ile | Ser | Cys | Leu | Thr | Phe | Gly | Arg |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Glu | Thr | Val | Leu | Glu | Tyr | Leu | Val | Ser | Phe | Gly | Val | Trp | Ile | Arg | Thr |
|-----|-----|-----|-----|-----|-----|-----|-----|-----|-----|-----|-----|-----|-----|-----|-----|
|     |     | 115 |     |     |     |     | 120 |     |     |     |     | 125 |     |     |     |

| Pro | Pro | Ala | Tyr | Arg | Pro | Pro | Asn | Ala | Pro | Ile | Leu | Ser | Thr | Leu | Pro |
|-----|-----|-----|-----|-----|-----|-----|-----|-----|-----|-----|-----|-----|-----|-----|-----|
|     | 130 |     |     |     |     | 135 |     |     |     |     | 140 |     |     |     |     |

| Glu | Thr | Thr | Val | Val | Arg | Arg | Arg | Asp | Arg | Gly | Arg | Ser | Pro | Arg | Arg |
|-----|-----|-----|-----|-----|-----|-----|-----|-----|-----|-----|-----|-----|-----|-----|-----|
| 145 |     |     |     |     | 150 |     |     |     |     | 155 |     |     |     |     | 160 |

| Arg | Thr | Pro | Ser | Pro | Arg | Arg | Arg | Arg | Ser | Gln | Ser | Pro | Arg | Arg | Arg |
|-----|-----|-----|-----|-----|-----|-----|-----|-----|-----|-----|-----|-----|-----|-----|-----|
|     |     |     |     | 165 |     |     |     |     | 170 |     |     |     |     | 175 |     |

| Arg | Ser | Gln | Ser | Arg | Glu | Ser | Gln | Cys |
|-----|-----|-----|-----|-----|-----|-----|-----|-----|
|     |     |     | 180 |     |     |     |     | 185 |

(2) INFORMATION FOR SEQ ID NO:9:

(i) SEQUENCE CHARACTERISTICS:
        (A) LENGTH: 558 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..558

(xi) SEQUENCE DESCRIPTION: SEQ ID NO:9:

| ATG | GCT | ATT | GAC | CCT | TAT | AAA | GAA | TTT | GGA | GCT | ACT | GTG | GAG | TTA | CTC | 48 |
|-----|-----|-----|-----|-----|-----|-----|-----|-----|-----|-----|-----|-----|-----|-----|-----|----|
| Met | Ala | Ile | Asp | Pro | Tyr | Lys | Glu | Phe | Gly | Ala | Thr | Val | Glu | Leu | Leu |    |
| 1   |     |     |     | 5   |     |     |     |     | 10  |     |     |     |     | 15  |     |    |

| TCG | TTT | TTG | CCT | TCT | GAC | TTC | TTT | CCT | TCC | GTC | AGA | GAT | CTC | CTA | GAC | 96 |
|-----|-----|-----|-----|-----|-----|-----|-----|-----|-----|-----|-----|-----|-----|-----|-----|----|
| Ser | Phe | Leu | Pro | Ser | Asp | Phe | Phe | Pro | Ser | Val | Arg | Asp | Leu | Leu | Asp |    |
|     |     |     | 20  |     |     |     |     | 25  |     |     |     |     | 30  |     |     |    |

| ACC | GCC | TCA | GCT | CTG | TAT | CGG | GAA | GCC | TTA | GAG | TCT | CCT | GAG | CAT | TGC | 144 |
|-----|-----|-----|-----|-----|-----|-----|-----|-----|-----|-----|-----|-----|-----|-----|-----|-----|
| Thr | Ala | Ser | Ala | Leu | Tyr | Arg | Glu | Ala | Leu | Glu | Ser | Pro | Glu | His | Cys |     |
|     |     | 35  |     |     |     |     | 40  |     |     |     |     | 45  |     |     |     |     |

| TCA | CCT | CAC | CAT | ACC | GCA | CTC | AGG | CAA | GCC | ATT | CTC | TGC | TGG | GGG | GAA | 192 |
|-----|-----|-----|-----|-----|-----|-----|-----|-----|-----|-----|-----|-----|-----|-----|-----|-----|
| Ser | Pro | His | His | Thr | Ala | Leu | Arg | Gln | Ala | Ile | Leu | Cys | Trp | Gly | Glu |     |
|     | 50  |     |     |     |     | 55  |     |     |     |     | 60  |     |     |     |     |     |

| TTG | ATG | ACT | CTA | GCT | ACC | TGG | GTG | GGT | AAT | AAT | TTG | GAA | GAT | CCA | GCA | 240 |
|-----|-----|-----|-----|-----|-----|-----|-----|-----|-----|-----|-----|-----|-----|-----|-----|-----|
| Leu | Met | Thr | Leu | Ala | Thr | Trp | Val | Gly | Asn | Asn | Leu | Glu | Asp | Pro | Ala |     |
| 65  |     |     |     |     | 70  |     |     |     |     | 75  |     |     |     |     | 80  |     |

| TCA | AGG | GAC | CTA | GTA | GTC | AAT | TAT | GTT | AAT | ACT | AAC | ATG | GGT | TTA | AAA | 288 |
|-----|-----|-----|-----|-----|-----|-----|-----|-----|-----|-----|-----|-----|-----|-----|-----|-----|
| Ser | Arg | Asp | Leu | Val | Val | Asn | Tyr | Val | Asn | Thr | Asn | Met | Gly | Leu | Lys |     |
|     |     |     |     | 85  |     |     |     |     | 90  |     |     |     |     | 95  |     |     |

| ATT | AGG | CAA | CTA | TTG | TGG | TTT | CAT | ATA | TCT | TGC | CTT | ACT | TTT | GGA | AGA | 336 |
|-----|-----|-----|-----|-----|-----|-----|-----|-----|-----|-----|-----|-----|-----|-----|-----|-----|
| Ile | Arg | Gln | Leu | Leu | Trp | Phe | His | Ile | Ser | Cys | Leu | Thr | Phe | Gly | Arg |     |
|     |     |     | 100 |     |     |     |     | 105 |     |     |     |     | 110 |     |     |     |

| GAG | ACT | GTA | CTT | GAA | TAT | TTG | GCC | TCT | TTC | GGA | GTG | TGG | ATT | CGC | ACT | 384 |
|-----|-----|-----|-----|-----|-----|-----|-----|-----|-----|-----|-----|-----|-----|-----|-----|-----|
| Glu | Thr | Val | Leu | Glu | Tyr | Leu | Ala | Ser | Phe | Gly | Val | Trp | Ile | Arg | Thr |     |
|     |     | 115 |     |     |     |     | 120 |     |     |     |     | 125 |     |     |     |     |

| CCT | CCA | GCC | TAT | AGA | CCA | CCA | AAT | GCC | CCT | ATC | TTA | TCA | ACA | CTT | CCG | 432 |
|-----|-----|-----|-----|-----|-----|-----|-----|-----|-----|-----|-----|-----|-----|-----|-----|-----|
| Pro | Pro | Ala | Tyr | Arg | Pro | Pro | Asn | Ala | Pro | Ile | Leu | Ser | Thr | Leu | Pro |     |
|     | 130 |     |     |     |     | 135 |     |     |     |     | 140 |     |     |     |     |     |

| GAA | ACT | ACT | GTT | GTT | AGA | CGA | CGG | GAC | CGA | GGC | AGG | TCC | CCT | AGA | AGA | 480 |
|-----|-----|-----|-----|-----|-----|-----|-----|-----|-----|-----|-----|-----|-----|-----|-----|-----|
| Glu | Thr | Thr | Val | Val | Arg | Arg | Arg | Asp | Arg | Gly | Arg | Ser | Pro | Arg | Arg |     |
| 145 |     |     |     |     | 150 |     |     |     |     | 155 |     |     |     |     | 160 |     |

| AGA | ACT | CCC | TCG | CCT | CGC | AGA | CGC | AGA | TCT | CAA | TCG | CCG | CGT | CGC | AGA | 528 |
|-----|-----|-----|-----|-----|-----|-----|-----|-----|-----|-----|-----|-----|-----|-----|-----|-----|
| Arg | Thr | Pro | Ser | Pro | Arg | Arg | Arg | Arg | Ser | Gln | Ser | Pro | Arg | Arg | Arg |     |
|     |     |     |     | 165 |     |     |     |     | 170 |     |     |     |     | 175 |     |     |

| AGA | TCT | CAA | TCT | CGG | GAA | TCT | CAA | TGT | TAG | 558 |
|-----|-----|-----|-----|-----|-----|-----|-----|-----|-----|-----|
| Arg | Ser | Gln | Ser | Arg | Glu | Ser | Gln | Cys |     |     |

180 185

(2) INFORMATION FOR SEQ ID NO:10:

(i) SEQUENCE CHARACTERISTICS:
(A) LENGTH: 185 amino acids
(B) TYPE: amino acid
(D) TOPOLOGY: linear (xi) SEQUENCE DESCRIPTION: SEQ ID NO:10:

```
Met Ala Ile Asp Pro Tyr Lys Glu Phe Gly Ala Thr Val Glu Leu Leu
 1               5                  10                  15

Ser Phe Leu Pro Ser Asp Phe Phe Pro Ser Val Arg Asp Leu Leu Asp
             20                  25                  30

Thr Ala Ser Ala Leu Tyr Arg Glu Ala Leu Glu Ser Pro Glu His Cys
         35                  40                  45

Ser Pro His His Thr Ala Leu Arg Gln Ala Ile Leu Cys Trp Gly Glu
     50                  55                  60

Leu Met Thr Leu Ala Thr Trp Val Gly Asn Asn Leu Glu Asp Pro Ala
65                  70                  75                  80

Ser Arg Asp Leu Val Val Asn Tyr Val Asn Thr Asn Met Gly Leu Lys
                 85                  90                  95

Ile Arg Gln Leu Leu Trp Phe His Ile Ser Cys Leu Thr Phe Gly Arg
             100                 105                 110

Glu Thr Val Leu Glu Tyr Leu Ala Ser Phe Gly Val Trp Ile Arg Thr
         115                 120                 125

Pro Pro Ala Tyr Arg Pro Pro Asn Ala Pro Ile Leu Ser Thr Leu Pro
     130                 135                 140

Glu Thr Thr Val Val Arg Arg Arg Asp Arg Gly Arg Ser Pro Arg Arg
145                 150                 155                 160

Arg Thr Pro Ser Pro Arg Arg Arg Arg Ser Gln Ser Pro Arg Arg Arg
                 165                 170                 175

Arg Ser Gln Ser Arg Glu Ser Gln Cys
             180                 185
```

(2) INFORMATION FOR SEQ ID NO:11:

(i) SEQUENCE CHARACTERISTICS:
(A) LENGTH: 645 base pairs
(B) TYPE: nucleic acid
(C) STRANDEDNESS: double
(D) TOPOLOGY: linear (ix) FEATURE:
(A) NAME/KEY: CDS
(B) LOCATION: 1..645

(xi) SEQUENCE DESCRIPTION: SEQ ID NO:11:

```
ATG GCT ATT GAC CCT TAT AAA GAA TTT GGA GCT ACT GTG GAG TTA CTC    48
Met Ala Ile Asp Pro Tyr Lys Glu Phe Gly Ala Thr Val Glu Leu Leu
 1               5                  10                  15

TCG TTT TTG CCT TCT GAC TTC TTT CCT TCC GTC AGA GAT CTC CTA GAC    96
Ser Phe Leu Pro Ser Asp Phe Phe Pro Ser Val Arg Asp Leu Leu Asp
             20                  25                  30

ACC GCC TCA GCT CTG TAT CGG GAA GCC TTA GAG TCT CCT GAG CAT TGC   144
Thr Ala Ser Ala Leu Tyr Arg Glu Ala Leu Glu Ser Pro Glu His Cys
         35                  40                  45

TCA CCT CAC CAT ACC GCA CTC AGG CAA GCC ATT CTC TGC TGG GGG GAA   192
```

| | | | | | | | | | | | | | | | | |
|---|---|---|---|---|---|---|---|---|---|---|---|---|---|---|---|---|
|Ser|Pro|His|His|Thr|Ala|Leu|Arg|Gln|Ala|Ile|Leu|Cys|Trp|Gly|Glu| |
| |50| | | |55| | | | |60| | | | | | |

| | | | | | | | | | | | | | | | | |
|---|---|---|---|---|---|---|---|---|---|---|---|---|---|---|---|---|
|TTG|ATG|ACT|CTA|GCT|ACC|TGG|GTG|GGT|AAT|AAT|TTG|GAA|GAT|CCA|GCA|240|
|Leu|Met|Thr|Leu|Ala|Thr|Trp|Val|Gly|Asn|Asn|Leu|Glu|Asp|Pro|Ala| |
|65| | | | |70| | | | |75| | | | |80| |

| | | | | | | | | | | | | | | | | |
|---|---|---|---|---|---|---|---|---|---|---|---|---|---|---|---|---|
|TCA|AGG|GAC|CTA|GTA|GTC|AAT|TAT|GTT|AAT|ACT|AAC|ATG|GGT|TTA|AAA|288|
|Ser|Arg|Asp|Leu|Val|Val|Asn|Tyr|Val|Asn|Thr|Asn|Met|Gly|Leu|Lys| |
| | | | |85| | | | |90| | | | |95| | |

| | | | | | | | | | | | | | | | | |
|---|---|---|---|---|---|---|---|---|---|---|---|---|---|---|---|---|
|ATT|AGG|CAA|CTA|TTG|TGG|TTT|CAT|ATA|TCT|TGC|CTT|ACT|TTT|GGA|AGA|336|
|Ile|Arg|Gln|Leu|Leu|Trp|Phe|His|Ile|Ser|Cys|Leu|Thr|Phe|Gly|Arg| |
| | | |100| | | | |105| | | | |110| | | |

| | | | | | | | | | | | | | | | | |
|---|---|---|---|---|---|---|---|---|---|---|---|---|---|---|---|---|
|GAG|ACT|GTA|CTT|GAA|TAT|TTG|GTC|TCT|TTC|GGA|GTG|TGG|ATT|CGC|ACT|384|
|Glu|Thr|Val|Leu|Glu|Tyr|Leu|Val|Ser|Phe|Gly|Val|Trp|Ile|Arg|Thr| |
| | |115| | | | |120| | | | |125| | | | |

| | | | | | | | | | | | | | | | | |
|---|---|---|---|---|---|---|---|---|---|---|---|---|---|---|---|---|
|CCT|CCA|GCC|TAT|AGA|CCA|CCA|AAT|GCC|CCT|ATC|TTA|TCA|ACA|CTT|CCG|432|
|Pro|Pro|Ala|Tyr|Arg|Pro|Pro|Asn|Ala|Pro|Ile|Leu|Ser|Thr|Leu|Pro| |
|130| | | | |135| | | | |140| | | | | | |

| | | | | | | | | | | | | | | | | |
|---|---|---|---|---|---|---|---|---|---|---|---|---|---|---|---|---|
|GAA|ACT|ACT|GTT|GTT|AGA|CGA|CGG|ACC|GAG|GCA|GGT|CCC|CTA|GAA|GAA|480|
|Glu|Thr|Thr|Val|Val|Arg|Arg|Arg|Thr|Glu|Ala|Gly|Pro|Leu|Glu|Glu| |
|145| | | | |150| | | | |155| | | | |160| |

| | | | | | | | | | | | | | | | | |
|---|---|---|---|---|---|---|---|---|---|---|---|---|---|---|---|---|
|GAA|CTC|CCT|CGC|CTC|GCA|GAC|GCA|GAT|CTC|AAT|CGC|CGC|GTC|GCA|GAA|528|
|Glu|Leu|Pro|Arg|Leu|Ala|Asp|Ala|Asp|Leu|Asn|Arg|Arg|Val|Ala|Glu| |
| | | |165| | | | |170| | | | |175| | | |

| | | | | | | | | | | | | | | | | |
|---|---|---|---|---|---|---|---|---|---|---|---|---|---|---|---|---|
|GAT|CTC|AAT|CTC|GGG|AAT|CTC|AAT|GTT|AGA|AGC|TTC|CGA|CAA|AAC|CGC|576|
|Asp|Leu|Asn|Leu|Gly|Asn|Leu|Asn|Val|Arg|Ser|Phe|Arg|Gln|Asn|Arg| |
| | |180| | | | |185| | | | |190| | | | |

| | | | | | | | | | | | | | | | | |
|---|---|---|---|---|---|---|---|---|---|---|---|---|---|---|---|---|
|CTA|CTC|TCT|TCT|AAA|AGT|CGG|ACT|ATG|TCT|AAT|TTA|GTC|TTG|CGT|CTT|624|
|Leu|Leu|Ser|Ser|Lys|Ser|Arg|Thr|Met|Ser|Asn|Leu|Val|Leu|Arg|Leu| |
| |195| | | | |200| | | | |205| | | | | |

| | | | | | | |
|---|---|---|---|---|---|---|
|CGC|CAG|ACT|ATT|TTG|TCT|TAG|645|
|Arg|Gln|Thr|Ile|Leu|Ser| | |
|210| | | | |215| | |

(2) INFORMATION FOR SEQ ID NO:12:

(i) SEQUENCE CHARACTERISTICS:
        (A) LENGTH: 214 amino acids
        (B) TYPE: amino acid
        (D) TOPOLOGY: linear (xi) SEQUENCE DESCRIPTION: SEQ ID NO:12:

| | | | | | | | | | | | | | | | |
|---|---|---|---|---|---|---|---|---|---|---|---|---|---|---|---|
|Met|Ala|Ile|Asp|Pro|Tyr|Lys|Glu|Phe|Gly|Ala|Thr|Val|Glu|Leu|Leu|
|1| | | |5| | | | |10| | | | |15| |

| | | | | | | | | | | | | | | | |
|---|---|---|---|---|---|---|---|---|---|---|---|---|---|---|---|
|Ser|Phe|Leu|Pro|Ser|Asp|Phe|Phe|Pro|Ser|Val|Arg|Asp|Leu|Leu|Asp|
| | | |20| | | | |25| | | | |30| | |

| | | | | | | | | | | | | | | | |
|---|---|---|---|---|---|---|---|---|---|---|---|---|---|---|---|
|Thr|Ala|Ser|Ala|Leu|Tyr|Arg|Glu|Ala|Leu|Glu|Ser|Pro|Glu|His|Cys|
| | |35| | | | |40| | | | |45| | | |

| | | | | | | | | | | | | | | | |
|---|---|---|---|---|---|---|---|---|---|---|---|---|---|---|---|
|Ser|Pro|His|His|Thr|Ala|Leu|Arg|Gln|Ala|Ile|Leu|Cys|Trp|Gly|Glu|
| |50| | | |55| | | | |60| | | | | |

| | | | | | | | | | | | | | | | |
|---|---|---|---|---|---|---|---|---|---|---|---|---|---|---|---|
|Leu|Met|Thr|Leu|Ala|Thr|Trp|Val|Gly|Asn|Asn|Leu|Glu|Asp|Pro|Ala|
|65| | | | |70| | | | |75| | | | |80|

| | | | | | | | | | | | | | | | |
|---|---|---|---|---|---|---|---|---|---|---|---|---|---|---|---|
|Ser|Arg|Asp|Leu|Val|Val|Asn|Tyr|Val|Asn|Thr|Asn|Met|Gly|Leu|Lys|
| | | | |85| | | | |90| | | | |95| |

| | | | | | | | | | | | | | | | |
|---|---|---|---|---|---|---|---|---|---|---|---|---|---|---|---|
|Ile|Arg|Gln|Leu|Leu|Trp|Phe|His|Ile|Ser|Cys|Leu|Thr|Phe|Gly|Arg|
| | | |100| | | | |105| | | | |110| | |

| | | | | | | | | | | | | | | | |
|---|---|---|---|---|---|---|---|---|---|---|---|---|---|---|---|
|Glu|Thr|Val|Leu|Glu|Tyr|Leu|Val|Ser|Phe|Gly|Val|Trp|Ile|Arg|Thr|
| | |115| | | | |120| | | | |125| | | |

| | | | | | | | | | | | | | | | |
|---|---|---|---|---|---|---|---|---|---|---|---|---|---|---|---|
|Pro|Pro|Ala|Tyr|Arg|Pro|Pro|Asn|Ala|Pro|Ile|Leu|Ser|Thr|Leu|Pro|
|130| | | | |135| | | | |140| | | | | |

```
Glu  Thr  Thr  Val  Val  Arg  Arg  Arg  Thr  Glu  Ala  Gly  Pro  Leu  Glu  Glu
145                      150                 155                 160

Glu  Leu  Pro  Arg  Leu  Ala  Asp  Ala  Asp  Leu  Asn  Arg  Arg  Val  Ala  Glu
                    165                      170                 175

Asp  Leu  Asn  Leu  Gly  Asn  Leu  Asn  Val  Arg  Ser  Phe  Arg  Gln  Asn  Arg
               180                      185                      190

Leu  Leu  Ser  Ser  Lys  Ser  Arg  Thr  Met  Ser  Asn  Leu  Val  Leu  Arg  Leu
               195                 200                      205

Arg  Gln  Thr  Ile  Leu  Ser
          210
```

( 2 ) INFORMATION FOR SEQ ID NO:13:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

AACAGAATTC        10

( 2 ) INFORMATION FOR SEQ ID NO:14:

( i ) SEQUENCE CHARACTERISTICS:
        ( A ) LENGTH: 8 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

AACAGACC        8

( 2 ) INFORMATION FOR SEQ ID NO:15:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

GGCCATGGAC ATTGACCCTT ATAAA        25

( 2 ) INFORMATION FOR SEQ ID NO:16:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

GGCATGGTC ATTGACCCTT ATAAAGAATT TGGA        34

( 2 ) INFORMATION FOR SEQ ID NO:17:

( i ) SEQUENCE CHARACTERISTICS:

(A) LENGTH: 29 base pairs
(B) TYPE: nucleic acid
(C) STRANDEDNESS: single
(D) TOPOLOGY: linear (xi) SEQUENCE DESCRIPTION: SEQ ID NO:17:

CCGAATTCAT GGACATTGAC CCTTATAAA     29

(2) INFORMATION FOR SEQ ID NO:18:

(i) SEQUENCE CHARACTERISTICS:
(A) LENGTH: 29 base pairs
(B) TYPE: nucleic acid
(C) STRANDEDNESS: single
(D) TOPOLOGY: linear (xi) SEQUENCE DESCRIPTION: SEQ ID NO:18:

CCGAATTCAT GGTCATTGAC CCTTATAAA     29

(2) INFORMATION FOR SEQ ID NO:19:

(i) SEQUENCE CHARACTERISTICS:
(A) LENGTH: 30 base pairs
(B) TYPE: nucleic acid
(C) STRANDEDNESS: single
(D) TOPOLOGY: linear (xi) SEQUENCE DESCRIPTION: SEQ ID NO:19:

CGGAATTCGA TGGACATTGA CCCTTATAAA     30

(2) INFORMATION FOR SEQ ID NO:20:

(i) SEQUENCE CHARACTERISTICS:
(A) LENGTH: 31 base pairs
(B) TYPE: nucleic acid
(C) STRANDEDNESS: single
(D) TOPOLOGY: linear (xi) SEQUENCE DESCRIPTION: SEQ ID NO:20:

CGGAATTCGG ATGGACATTG ACCCTTATAA A     31

(2) INFORMATION FOR SEQ ID NO:21:

(i) SEQUENCE CHARACTERISTICS:
(A) LENGTH: 32 base pairs
(B) TYPE: nucleic acid
(C) STRANDEDNESS: single
(D) TOPOLOGY: linear (xi) SEQUENCE DESCRIPTION: SEQ ID NO:21:

CGGAATTCGG AATGGACATT GACCCTTATA AA     32

(2) INFORMATION FOR SEQ ID NO:22:

(i) SEQUENCE CHARACTERISTICS:
(A) LENGTH: 33 base pairs
(B) TYPE: nucleic acid
(C) STRANDEDNESS: single
(D) TOPOLOGY: linear (x i) SEQUENCE DESCRIPTION: SEQ ID NO:22:

CGGAATTCGG ATATGGACAT TGACCCTTAT AAA    33

(2) INFORMATION FOR SEQ ID NO:23:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (x i) SEQUENCE DESCRIPTION: SEQ ID NO:23:

CGGGAATTCG GATCATGGAC ATTGACCCTT ATAAA    35

(2) INFORMATION FOR SEQ ID NO:24:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (x i) SEQUENCE DESCRIPTION: SEQ ID NO:24:

GGAAGCTTCT AACATTGAGA TTCCCGAGAT TGAGATCTTC TGCG    44

What is claimed is:

1. A method for expressing HBcAg which comprises transforming a host with a vector comprising DNA having the sequence consisting essentially of Sequence ID No: 3, Sequence ID No: 5, Sequence ID No: 7, Sequence ID No: 9, or Sequence ID No: 11.

2. The method of claim 1 in which said sequences further comprise about an 8 to 20 base pair spacer 5' the initiation codon.

3. The method of claim 2 in which said spacer consists essentially of Sequence ID No: 13.

4. The method of claim 1 in which said spacer consists essentially of Sequence ID No: 14.

5. The method of claim 1 in which the second codon of said sequence is a host preferred codon.

6. The method of claim 2 in which the second codon of said sequence is a host preferred codon.

7. The method of claim 3 in which the second codon of said sequence is a host preferred codon.

8. The method of claim 4 in which the second codon of said sequence is a host preferred codon.

9. The method of claim 5 in which said preferred codon is an *E. coli* preferred codon.

10. The method of claim 6 in which said preferred codon is an *E. coli* preferred codon.

11. The method of claim 7 in which said preferred codon is an *E. coli* preferred codon.

12. The method of claim 8 in which said preferred codon is an *E. coli* preferred codon.

13. A method for expressing HBcAg which comprises transforming a host with a vector comprising DNA having the sequence consisting essentially of Sequence ID No: 13: 5' to the sequence consisting essentially of Sequence ID No: 5.

* * * * *